US011013790B2

(12) United States Patent
Mach

(10) Patent No.: US 11,013,790 B2
(45) Date of Patent: May 25, 2021

(54) VACCINATION WITH IMMUNO-ISOLATED CELLS PRODUCING AN IMMUNOMODULATOR

(71) Applicant: MaxiVAX SA, Geneva (CH)

(72) Inventor: Nicolas Mach, Collonge-Bellerive (CH)

(73) Assignee: MaxiVAX SA, Geneva (CH)

( * ) Notice: Subject to any disclaimer, the term of this patent is extended or adjusted under 35 U.S.C. 154(b) by 541 days.

(21) Appl. No.: 15/276,016

(22) Filed: Sep. 26, 2016

(65) Prior Publication Data

US 2017/0087234 A1 Mar. 30, 2017

Related U.S. Application Data

(60) Provisional application No. 62/232,940, filed on Sep. 25, 2015, provisional application No. 62/384,416, filed on Sep. 7, 2016.

(51) Int. Cl.
| | |
|---|---|
| *A61K 35/15* | (2015.01) |
| *A61K 39/00* | (2006.01) |
| *A61K 39/39* | (2006.01) |
| *A61K 45/06* | (2006.01) |
| *A61M 5/178* | (2006.01) |
| *C12N 5/09* | (2010.01) |
| *A61K 9/00* | (2006.01) |
| *A61K 9/48* | (2006.01) |
| *C12P 21/00* | (2006.01) |

(52) U.S. Cl.
CPC ........ *A61K 39/0011* (2013.01); *A61K 9/0019* (2013.01); *A61K 9/4891* (2013.01); *A61K 39/39* (2013.01); *A61K 45/06* (2013.01); *A61M 5/178* (2013.01); *C12N 5/0693* (2013.01); *C12P 21/005* (2013.01); *A61K 2039/515* (2013.01); *A61K 2039/5152* (2013.01); *A61K 2039/54* (2013.01); *A61K 2039/55522* (2013.01); *A61K 2039/6093* (2013.01); *A61M 2202/30* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,680,174 | A | 7/1987 | Javis, Jr. et al. |
| 5,637,483 | A | 6/1997 | Dranoff et al. |
| 5,679,356 | A | 10/1997 | Bonnem et al. |
| 5,861,159 | A | 1/1999 | Pardoll et al. |
| 5,904,920 | A | 5/1999 | Dranoff et al. |
| 5,955,095 | A | 9/1999 | Gentile et al. |
| 6,193,970 | B1 | 2/2001 | Pardoll et al. |
| 6,916,640 | B2 | 7/2005 | Yu et al. |
| 7,250,291 | B1 | 7/2007 | Dranoff et al. |
| 2001/0043923 | A1* | 11/2001 | Schinstine ......... A01K 67/0275 424/93.21 |
| 2005/0118425 | A1 | 6/2005 | Childs et al. |
| 2014/0341982 | A1 | 11/2014 | Mach |

FOREIGN PATENT DOCUMENTS

| | | |
|---|---|---|
| EP | 1 159 967 | 12/2001 |
| WO | WO 96/02646 | 2/1996 |
| WO | WO 98/16246 | 4/1998 |
| WO | WO 98/33520 | 8/1998 |
| WO | WO 99/38954 | 8/1999 |
| WO | WO 02/080972 | 10/2002 |
| WO | WO 2003/105895 | 12/2003 |

OTHER PUBLICATIONS

Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin", J. Protein Chem. 11 (5): 433-44 (1992).
Aruga et al., "Reduced Efficacy of Allogeneic versus Syngeneic Fibroblasts Modified to Secrete Cytokines as a Tumor Vaccine Adjuvant", Cancer Research, 57: 3230-3237 (1997).
Bar et al., "Inhibition of tumor growth by the continuous delivery of IL-1 receptor antagonist (IL-1Ra) from microencapsulated genetically-engineered cells", J. Controlled Release, 72:228-229 (2001).
Bessis et al., "Encapsulation in hollow fibres of xenogeneic cells engineered to secrete IL-4 or IL-13 ameliorates murine collagen-induced arthritis (CIA)", Clin. Exp. Immunol., 177:376-382 (1999).
Billington, W.D., "Maternal Immune Response to Pregnancy", Reprod. Fertil. Dev., 1 (3):183-190 (1989).
Bonazzi et al., "Bacterial entry into cells: A role for the endocytic machinery", FEBS Lett., 580( 12):2962-2967 (2006).
Borrello et al., "A Universal Granulocyte-Macrophage Colony-Stimulating Factor-Producing Bystander Cell Line for Use in the Formulation of Autologous Tumor Cell-Based Vaccines," Human Gene Therapy, 10:1983-1991 (1999).
Cirone et al., "Immuno-Isolation in Oncology—A Mini-Review", Curr. Pharm. Biotechnol., 2:269-277 (2001).
Cohen et al., "Pronounced acute immunosuppression in Vivo mediated by HIV Tat challenge", Proc. Natl. Acad. Sci. USA, 96:10842-10847 (1999).
Cotran et al., "Viral and Microbial Carcinogenesis: DNA Oncogenic Viruses" in Pathologic Basis of Disease, Sixth Edition, pp. 311-314 (1999).
Crystal, R.G., "Transfer of Genes to Humans: Early Lessons and Obstacles to Success", Science, 270:404-410 (1995).

(Continued)

*Primary Examiner* — Michael D Pak
(74) *Attorney, Agent, or Firm* — Saliwanchik, Lloyd & Eisenschenk

(57) ABSTRACT

Provided herein are vaccine compositions containing at least one retrievable biocompatible macrocapsule containing immuno-isolated allogeneic cells that secrete an immuno-modulator such as GM-CSF (granulocyte-macrophage colony stimulating factor) and an antigenic component such as autologous tumor cells or infectious agents. Also provided are kits and pharmaceutical compositions containing the vaccine compositions as well as methods of use thereof for therapeutic or preventative vaccination against tumors or infectious agents.

14 Claims, 14 Drawing Sheets

(56) References Cited

OTHER PUBLICATIONS

Danos et al., "Safe and efficient generation of recombinant retroviruses with amphotropic and ecotropic host ranges", Proc. Natl. Acad. Sci. USA, 85:6460-6464 (1988).
Database BIOSIS 'Online', Biosciences Information Service, Philadelphia, PA, US; Nov. 16, 2000, McNall Rene et al., "Tumor vaccines with cytokine secreting bystander cells in murine AML", Database accession No. PREV200100299398 (Abstract) & Blood, 42nd Annual Meeting of the American Society of Hematology, San Francisco, CA, 96(11 ):122a (Abstract # 526) (2000).
Dranoff et al., "Vaccination with irradiated tumor cells engineered to secrete murine granulocyte-macrophage colony-stimulating factor stimulates potent, specific, and long-lasting anti-tumor immunity", Proc. Natl. Acad. Sci. USA, 90:3539-3543 (1993).
Fox, J.L., "No winners against AIDS", Biotechnol., 12:128 (1994).
Gura, T., "Systems for Identifying New Drugs are Often Faulty", Science, 278:1041-1042 (1997).
Illustrated Dictionary of Immunology, CRC Press, Inc., Vaccine (1995).
Jaffee et al., "High Efficiency Gene Transfer into Primary Human Tumor Explants without Cell Selection", Cancer Res., 53:2221-2226 (1993).
Jaffee et al., "Novel Allogeneic Granulocyte-macrophage Colony-Stimulating Factor-Secreting Tumor Vaccine for Pancreatic Cancer: A Phase I Trial of Safety and Immune Activation", J. Clin. Oncol., 19(1): 145-156 (2001).
La Temple et al., "Increased Immunogenicity of Tumor Vaccines Complexed with Anti-Gal: Studies in Knockout Mice for α1,3Galactosyltransferase", Cancer Res., 59:3417-3423 (1999).
Lu et al., "Pregnancy as a natural model of allograft tolerance. Interactions between Adherent Macrophages and Trophoblast Populations", Transplantation, 48(5):848-855 (1989).
Mach et al., "Differences in Dendritic Cells Stimulated in Vivo by Tumors Engineered to Secrete Granulocyte-Macrophage Colony-stimulating Factor or Flt3-Ligand", Cancer Research, 60:3239-3246 (2000).
Mach et al., "Cytokine-secreting tumor cell vaccines", Curr Opin Immunol, 12:571-575 (2000).
Neumanaitis et al., "Granulocyte—Macrophage Colony-Stimulating Factor Gene-Modified Autologous Tumor Vaccines in Non-Small-Cell Lung Cancer", Journal of the National Cancer Institute, 96(4):326-31 (2004).
Ory et al., "A stable human-derived packaging cell line for production of high titer retrovirus/vesicular stomatitis virus G pseudotypes", Proc. Natl. Acad. Sci. USA, 93:11400-11406 (1996).
Paul, W.E., "Vaccines" in Fundamental Immunology, Raven Press, Ltd., pp. 1311-1312 (1993).

Riffkin et al., "A single amino-acid change between the antigenically different extracellular serine proteases V2 and B2 from Dichelobacter nodosus", Gene, 167:279-283 (1995).
Salgia et al., "Vaccination With Irradiated Autologous Tumor Cells Engineered to Secrete Granulocyte-Macrophage Colony-Stimulating Factor Augments Antitumor Immunity in Some Patients With Metastatic Non-Small-Cell Lung Carcinoma", J Clin Oncol, 21:624-30 (2003).
Schilbach et al., "Human γδ T Lymphocytes Exert Natural and IL-2-Induced Cytotoxicity to Neuroblastoma Cells", J. Immunother., 23:536-548 (2000).
Shao et al., "Delivery of Cytokines by Microencapsulated Transduced Cells", Proc. Int. Symp. Control. Release. Bioact. Mater., 21:46-47 (1994).
Shehu-Xhilaga et al., "Antiretroviral Compounds: Mechanisms Underlying Failure of HAART to Eradicate HIV-1", Curr. Med. Chem., 12(15):1705-1719 (2005).
Simons et al., "Induction of Immunity to Prostate Cancer Antigens: Results of a Clinical Trial of Vaccination with Irradiated Autologous Prostate Tumor Cells Engineered to Secrete Granulocyte-Macrophage Colony-stimulating Factor Using ex Vivo Gene Transfer", Cancer Res., 59(20):5160-5168 (1999).
Simons, "Bioactivity of human GM-CSF gene therapy in metastatic renal cell carcinoma and prostate cancer", Acta Ural. Jpn., 43(11):821-822 (1997).
Soiffer et al, "Vaccination with irradiated autologous melanoma cells engineered to secrete human granulocyte-macrophage colony-stimulating factor generates potent antitumor immunity in patients with metastatic melanoma", Proc. Natl. Acad. Sci. USA, 95:13141-13146 (1998).
Soiffer et al., "Vaccination with Irradiated, Autologous Melanoma Cells Engineered to Secrete Granulocyte-Macrophage Colony-Stimulating Factor by Adenoviral-Mediated Gene Transfer Augments Antitumor Immunity in Patients with Metastatic Melanoma", J Clin Oncol, 21:3343-3350 (2003).
Tait et al., "Ovarian Cancer *BRCA1* Gene Therapy: Phase I and II Trial Differences in Immune Response and Vector Stability", Clin. Cancer Res., 5:1708-1714 (1999).
Teshima et al. "Tumor Cell Vaccine Elicits Potent Antitumor Immunity after Allogeneic T-Cell-depleted Bone Marrow Transplantation", Cancer Research, 61:162-171 (2001).
Von Mehren et al., "The Influence of Granulocyte Macrophage Colony-Stimulating Factor and Prior Chemotherapy on the Immunological Response to a Vaccine (ALVAC-CEA B7.1) in Patients with Metastatic Carcinoma", Clin. Cancer Res., 7(5):1181-1191 (2001).
Weinberg et al., "Are Viral-Encoded MicroRNAs Mediating Latent HIV-1 Infection?", DNA Cell Biol., 25(4):223-231 (2006).
Schwenter F. et al. "Cell encapsulation technology as a novel strategy for human anti-tumor immunotherapy", Cancer Gene Therapy, vol. 18, 2011, pp. 553-562.

\* cited by examiner

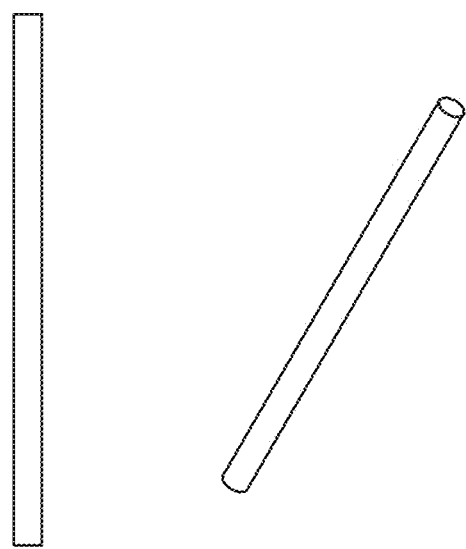
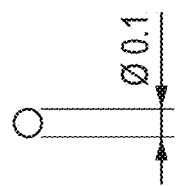
Figure 1D

Figure 4

Figure 7A

| Project # | Cmpd Name | Pathway | Cell Line Tested | Cell Line Part# / Lot# |
|---|---|---|---|---|
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0276 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |
| SSCL12365_36744 | 017-0281 | STAT5 | STAT5 TF-1 | KV1598A/50405 |

Figure 7B

| Modification Event | EC50 (nM) | Hillslope | R² Value | [Cmpd] (nM) | % Activation Point 1 | Point 2 |
|---|---|---|---|---|---|---|
| STAT5 A/B [pTyr694/699] | 0.0789 | 1.85 | 0.9946 | 1.43 | 234 | 97 |
| STAT5 A/B [pTyr694/699] | 0.0789 | 1.85 | 0.9946 | 0.452 | 172 | 103 |
| STAT5 A/B [pTyr694/699] | 0.0789 | 1.85 | 0.9946 | 0.143 | 91 | 63 |
| STAT5 A/B [pTyr694/699] | 0.0789 | 1.85 | 0.9946 | 0.0452 | 26 | 31 |
| STAT5 A/B [pTyr694/699] | 0.0789 | 1.85 | 0.9946 | 0.0143 | 15 | 11 |
| STAT5 A/B [pTyr694/699] | 0.0789 | 1.85 | 0.9946 | 0.00452 | 7 | 6 |
| STAT5 A/B [pTyr694/699] | 0.0789 | 1.85 | 0.9946 | 0.00143 | 3 | 5 |
| STAT5 A/B [pTyr694/699] | 0.0789 | 1.85 | 0.9946 | 0.000450 | 5 | -3 |
| STAT5 A/B [pTyr694/699] | 0.0789 | 1.85 | 0.9946 | 0.000140 | 2 | 7 |
| STAT5 A/B [pTyr694/699] | 0.0789 | 1.85 | 0.9946 | 0.0000400 | 1 | 3 |
| STAT5 A/B [pTyr694/699] | 0.147 | 1.51 | 0.9804 | 1.43 | 268 | 166 |
| STAT5 A/B [pTyr694/699] | 0.147 | 1.51 | 0.9804 | 0.452 | 160 | 179 |
| STAT5 A/B [pTyr694/699] | 0.147 | 1.51 | 0.9804 | 0.143 | 77 | 77 |
| STAT5 A/B [pTyr694/699] | 0.147 | 1.51 | 0.9804 | 0.0452 | 37 | 49 |
| STAT5 A/B [pTyr694/699] | 0.147 | 1.51 | 0.9804 | 0.0143 | 6 | 12 |
| STAT5 A/B [pTyr694/699] | 0.147 | 1.51 | 0.9804 | 0.00452 | -2 | 3 |
| STAT5 A/B [pTyr694/699] | 0.147 | 1.51 | 0.9804 | 0.00143 | 10 | 10 |
| STAT5 A/B [pTyr694/699] | 0.147 | 1.51 | 0.9804 | 0.000450 | 4 | 5 |
| STAT5 A/B [pTyr694/699] | 0.147 | 1.51 | 0.9804 | 0.000140 | -1 | 5 |
| STAT5 A/B [pTyr694/699] | 0.147 | 1.51 | 0.9804 | 0.0000400 | 2 | -4 |

Figure 7D

| Control Cmpd Name | Control EC50 (nM) |
|---|---|
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |
| GM-CSF | 0.00817 |

VACCINATION WITH IMMUNO-ISOLATED CELLS PRODUCING AN IMMUNOMODULATOR

RELATED APPLICATIONS

This application claims priority to U.S. Application Ser. No. 62/232,940, filed Sep. 25, 2015 and to U.S. Application No. 62/384,416, filed Sep. 7, 2016, the contents of each of which are herein incorporated by reference in their entities.

FIELD OF THE INVENTION

The present invention relates to generally to the field of immunology, in particular cell based-immunization against tumors and vaccination against infectious agents.

BACKGROUND OF THE INVENTION

In the field of vaccination, first generation vaccines contained only the antigen against which an immune response was desired. However, because the presence of an antigen alone is in most cases only weakly efficient, a second generation of vaccines was developed, where the vaccinating composition included one or more adjuvants as immunomodulators (i.e., GM-CSF alone or in combination with other adjuvants) to enhance this immune response. In order to be effective, the adjuvant must be stably released at the vaccination site for several days.

Several different techniques have been reported for providing the adjuvant at the vaccination site, and the choice of the technique depends on the context of the immunization.

For example, in the context of antigen-based vaccines (as opposed to cell-based vaccines), a widely applicable technique is simply to combine the antigen with the adjuvant in the vaccinating composition. The resulting composition is administered directly to the subject, thereby supplying the antigen and adjuvant in a simultaneous and co-localized manner.

However, this simple approach cannot be used in all vaccination settings. For example, in most cancers (e.g., lung, colon, stomach, lymphoma, and brain), useful antigens for vaccination are often not known. Therefore, for these types of cancer, cell-based immunization strategies against tumors are needed. For immunization strategies involving cell-based vaccines, the antigen(s) is produced by whole cells, which are implanted in a subject. Such strategies require the use of more elaborate techniques to ensure the efficient delivery of the adjuvant.

In one example, the immunomodulator is directly injected at the vaccination site, either in a "naked" form or in a slow release formulation using pegylated, liposomal microspheres. However, this strategy is often limited by technical and biochemical difficulties, as systemic administration of the adjuvant is not efficient and may be toxic and local release of recombinant proteins being used as an adjuvant (i.e., GM-CSF) is not reliable because GM-CSF is an unstable protein that has a half-life of only a few hours within the human body. Thus, in order to be effective, GM-CSF has to be continuously produced in situ in order to be therapeutically effective.

Another example used to circumvent the problems arising from the direct injection technique is the use of "bystander cells" to locally produce the immunomodulators. In these methods, cells producing the required adjuvant are implanted in proximity to the source of the antigen, thereby providing an efficient, local release of adjuvant at the vaccine site.

However, this approach also has some drawbacks. For human immunization, multiple immunizations are required, and, because syngeneic bystander cells are not readily available, allogenic cells are most often used. Thus, after the first injection, the bystander cells are recognized by the immune system of the host (allorecognition) and are rejected, thereby preventing further stable and sustained production of immunomodulator and jeopardizing the desired immune response against the antigenic substance of the vaccine.

In order to overcome this allorecognition problem, Borrello et al (*Human Gene Therapy,* 1999, 10(12), 1983-1991) described a strategy in which the GM-CSF-supplying cell is a cell line, K-562 (ATCC Deposit No. CCL-243), which do not express MCH molecules on their surface and fail to express HLA class I or II antigens, thereby potentially decreasing the magnitude of the alloresponses generated on repeated immunizations. However, these cells are human cancer cells and are highly sensitive to potent rejection mechanisms that occur without the involvement of HLA class I or II proteins that are less specific but are very rapid and potent for cellular destruction. For example, K-562 cells are known to be very sensitive to NK cells and also to $\gamma\delta$ T cells leading to rapid elimination of allogeneic cells.

Therefore, it is likely that K-562 bystander cells injected at the vaccine site will be destroyed efficiently and quickly by non-MHC dependent cytotoxic mechanisms, which may significantly decrease the release of the immunomodulator.

Moreover, in addition to being very sensitive to rapid destruction by NK cells, K-562 cells can also express MHC class I upon interferon $\gamma$ exposure. Because interferon $\gamma$ could be present or released at the vaccination site during the first or after repeated immunizations, such MHC class I upregulation will also lead to rapid cell destruction via classical cellular immunity.

For these reasons, use of cells such as K-562 in vaccination is associated with numerous drawbacks.

Another solution that is widely used in the context of cell-based vaccines is to couple the production of antigen and the release of immunomodulator by engineering the cell that is the source of antigen to also supply the immunomodulator. For example, in cancer vaccines, the source of antigen is usually a whole tumor cell, which can be engineered, for example by transfection, to simultaneously produce the necessary adjuvant.

In view of the favorable results obtained in the mouse model, the initial human trials used the same strategy. However, the technique proved to be very labor intensive and time consuming because the patient's surgically harvested cells need to be expanded in vitro for retroviral infection, thereby preventing a wide use of the method.

The use of other viral vectors to infect the tumor cells has also been proposed to circumvent the difficulties observed with the use of retroviral vectors.

Nevertheless, the major problem associated with the new viruses tested is that, in most cases, some viral proteins will be expressed from the tumor cells after infection, and these viral proteins are strongly recognized by the immune system as foreign, infectious agents. Therefore, the initial goal of mounting an immune response against weak tumor antigens is skewed or diverted towards a viral protein, which results in masking the anti-tumor immune response and priming the recipient against subsequent immunization, which will further increase the destruction of the injected cells and will likely decrease the efficacy of the anti-tumor immunization scheme.

Thus, while the use of autologous engineered tumor cells as combined source of antigen and adjuvant a priori minimizes the risk of undesirable immune response, the step of viral infection itself gives rise to significant problems.

In order to limit the problems arising from viral infection of autologous cells, new strategies have been developed which do not require the patients' cells. In these techniques, the antigenic source is provided by cell lines derived from other patients with similar type of cancer, and the patient is immunized with repeated injections of irradiated, GM-CSF secreting, allogeneic (from another human being) tumor cells. The percentage of patients showing an immune response in studies using these techniques has been lower than expected.

Accordingly, there remains a need in the art to develop vaccine compositions that provide both a constant source of immunomodulator and an antigenic component that is substantially free of undesirable interactions with the natural or adaptative immune system.

SUMMARY OF THE INVENTION

The development of a good antigen-driven cancer immunotherapy requires the proper location, the proper antigenic material (i.e., autologous tumor cells), the proper immunostimulatory signal (for example, GM-CSF (alone or in combination with other adjuvants), the sustained delivery of the necessary adjuvant, the stable and reproducible delivery of adjuvant and antigenic component, the availability of clinical grade material, as well as the ability to scale up production. Potent anticancer immunization requires tumor-specific antigens and strong adjuvant. Local, stable release of an immunomodulator such as GM-CSF over days at the immunization site is among the strongest adjuvants. It induces potent, long-lasting, specific anti-tumor immunity in all murine cancer types tested. However, systemic delivery of GM-CSF is not a good adjuvant, as it recruits MSDC and does not boost cancer immunity.

Using encapsulated cell therapy (ECT), a subcutaneous clinical grade platform has been generated. The present invention relates to a clinical grade immunization strategy that utilizes two component vaccine compositions. One component of the vaccine composition is an antigenic component (i.e., lethally irradiated autologous tumor cells or one or more infectious agents), while the other component is at least one retrievable biocompatible macrocapsule that contains immuno-isolated allogeneic cells that secrete or that have been genetically engineered to secrete an effective amount of an immunomodulatory agent (i.e., GM-CSF) for a period of at least one week. These immuno-isolated allogeneic cells secrete an active form of the immunomodulator in a continuous and non-immunogenic manner in the immediate vicinity of the antigenic component.

The present invention provides a new approach that overcomes the drawbacks associated with previous immunization strategies and is based on the compositions and methods described in WO 2003/105895, which is herein incorporated by reference in its entirety.

The vaccination strategies described herein do not require any custom made gene therapy protocols and do not involve the use of any viral vectors. Rather, a standardized adjuvant (i.e., GM-CSF) is released from the macrocapsules subcutaneously in close proximity to the antigenic component. This cell-based immunotherapy combines sustained, stable, standardized local release of GM-CSF and tumor specific antigens.

Any of the vaccine compositions described herein can be used for therapeutic or preventative vaccination for cancer therapy or treatment (also referred to interchangeably herein as Onco-Maxi-Vax or MVX-ONCO-1) or for infectious agent therapy or prevention (also referred to interchangeably herein as Immuno-Maxi-Vax or IA-Maxi-Vax). Because the anticancer therapy is based on triggering the patient's own natural immune response mechanism in order to eliminate cancer cells, it can be used in all types of cancer, including both solid tumors and blood-related cancers.

Provided herein are vaccine compositions containing: (a) at least one retrievable biocompatible macrocapsule containing between about $1 \times 10^5$ and about $1 \times 10^6$ immuno-isolated allogeneic cells (e.g., about $8 \times 10^5$ immuno-isolated allogeneic cells) that secrete at least 20 ng/24 hour of GM-CSF and (b) an antigenic component, wherein the at least one biocompatible macrocapsule has a core containing the allogenic cells and an internal coil, wherein the allogeneic cells are distributed on the internal coil; and a semi-permeable membrane surrounding the core that permits diffusion of GM-CSF there through. Several different concentrations of allogeneic cells within the biocompatible macrocapsules were tested (e.g., 5, 8, 10 and $15 \times 10^5$ cells). In one non-limiting embodiment, $8 \times 10^5$ cells was selected because it offers the best long-term stability suitable for long-term release with minimal variability.

The semipermeable membrane is made of a material selected from the group consisting of polyethersulfone (PES) and thermoplastic polyurethane and/or the internal coil is made of aluminum or titanium. Several membrane thicknesses with several different pore sizes were tested (e.g., PES 5, UltraPES 0.8, Ultra PES 0.7). In some embodiments, the distance between the spires on the internal coil is about 1 mm±0.1 mm. The internal coil may be made from aluminum, titanium, or the like.

Each biocompatible capsule may be cylindrical in shape. In some embodiments each biocompatible macrocapsule is between 5 and 25 mm in length (i.e., about 5, 6, 7, 8, 9, 10, 11, 12, 13, 14, 15, 16, 17, 18, 19, 20, 21, 22, 23, 24, or 25 mm in length). Twelve mm was selected as the best size for implantation, handling, manufacturing, and cell loading procedures.

The macrocapsules may also contain a retrieval tube, which can be made from any suitable material, including, but not limited to, a polyurethane. The membrane of the at least one macrocapsule may be secured to the retrieval tube. For example, a connector (e.g., a stainless steel connector) can be used to secure the retrieval tube to the membrane of the at least one biocompatible macrocapsule. The end of the connector that is inserted into the membrane preferably has a truncated conical shape.

The retrieval tube may further contain a retrieval hook to facilitate retrieval of at least one macrocapsule after implantation. For example, the hook can be used to secure the macrocapsules during implantation and be used to remove the macrocapsules after a defined period of time.

In some embodiments, the retrieval hook contains an eyelet and at least two legs to facilitate attachment to the retrieval tube.

The retrieval hook can be made from any suitable material, including, but not limited to, stainless steel, and it can be secured to the retrieval tube using an ultraviolet curable glue.

A suture can be placed through the eyelet in order to secure the retrieval hook after implantation.

The at least one biocompatible macrocapsule further contains a loading hub to facilitate the loading of cells. In some embodiments, the loading hub has a truncated conical end. The loading hub may be friction fitted into the membrane.

In other embodiments, the at least one biocompatible macrocapsule is contained within a transport tube having a tube body and a tube cap that may contain one or more holes. Additionally, the tube cap may also contain a luer lock that is friction fitted into the cap. The loading hub may be matingly engaged into the luer lock within the cap.

In some embodiments, the vaccine composition contains two biocompatible macrocapsules.

The immuno-isolated allogeneic cells within each macrocapsule secretes at least 20 ng/24 h of GM-CSF for a period of at least one week.

In some embodiments, the antigenic component is autologous tumor cells that optionally may be irradiated. In these embodiments, the antigenic component is between about $1\times10^6$ and about $1\times10^7$ autologous tumor cells (e.g., about $4\times10^6$ autologous tumor cells). Lethally irradiated tumor cells can be stored frozen for long-term storage for up to 12 months (i.e., 1, 2, 3, 4, 5, 6, 7, 8, 9, 10, 11, or 12 months).

In other embodiments, the antigenic component is from an infectious agent (e.g., a virus, a bacterium, a parasitic pathogen, or a fungus). For example, suitable antigenic components include an inactivated pathogen, an infectious agent lysate, a protein extract, a recombinant protein, a peptide, or DNA. By way of non-limiting examples, the virus is selected from the group consisting of HIV, CMV, recurrent herpes infection, Hepatitis B, Epstein Bar virus, Hepatitis C, and human papilloma virus (HPV); the bacterium is selected from the group consisting of mycobacterial infection, *Helicobacter pylori*, and meningococcal infection; the parasitic pathogen is selected from the group consisting of malaria, toxoplasma, Pneumocystis, and echinococcosis; and/or the fungus is selected from the group consisting of candida and aspergillus.

In any of the vaccine compositions described herein, the immune-isolated allogeneic cells further secrete at least one additional immunomodulatory agent (e.g., IL-12, IL-15, IL-4, interferon gamma, chemokines or dendritic cells growth factors, IL-3, IL-9, IL-1, IL-2, IL-7, transmembrane receptors of IFNγ. Stem Cell Factor (SCF) soluble or membranous, FL (Flt3 Ligand), G-CSF, TLR7 agonists, T cell immunoglobulin mucin-3 (TIM-3), glucocorticoid-induced TNFR family related gene (GITR), lymphocyte-activation gene 3 (LAG-3), Vista, B- and T-lymphocyte attenuator (also known as CD272) (BTLA), inducible T-cell COStimulator (ICOS) (also known as CD278), tumor necrosis factor receptor superfamily member 4 (OX40) (also known as CD134 or TNFRSF4), CD40, CD137 (also known as 41BB), CD27, and combinations thereof).

The membrane surrounding the immuno-isolated allogeneic cells within the core of the macrocapsule is selectively permeable. For example, the molecular weight cut of (MWCO) of the membrane is approximately 280 kDa.

In some embodiments, the immuno-isolated allogeneic cells are genetically modified to express GM-CSF, for example by transfection by a plasmid or infection by a virus.

The immuno-isolated allogeneic cells are a human established cell line (e.g., non-adherent cell line such as a cell of hematopoietic origin). In some embodiments, the immuno-isolated allogeneic cells are immortal or immortalized and/or are non tumoral. The immuno-isolated allogeneic cells are of mammal origin (e.g., human or non-human mammal). In some embodiments, the immuno-isolated allogeneic cells are irradiated.

The immuno-isolated allogeneic cells secrete between about 80 and about $960\times10^{-15}$ g/24 hr of GM-CSF, more than $10\times10^{-15}$ g/24 hr of GM-CSF, or more than $100\times10^{-15}$ g/24 hr of GM-CSF.

In certain embodiments, the at least one biocompatible macrocapsule secretes between 50 and 150 ng/day (e.g., 50, 55, 60, 65, 70, 75, 80, 85, 90, 95, 100, 105, 110, 115, 120, 125, 130, 135, 140, 145, or 150 ng/day) of GM-CSF.

Any of the vaccine compositions described herein may also contain one or more additional therapeutic agents. In some embodiments, the one or more additional therapeutic agents are immune check-point modulators. For example, the immune check-point modulators may be products or agents (e.g., proteins, antibodies, compounds, etc.) that target one or more immunomodulatory molecules such as, for example, cytotoxic T-lymphocyte associated protein (CTLA-4), programmed cell death protein 1 (PD-1), programmed cell death protein 1 ligand (PD-L1), TIM-3, GITR, LAG-3, Vista, BTLA, ICOS, OX40, CD40, CD137 (also known as 41BB), CD27, indoleamine 2,3 dioxygenase (IDO), and combinations thereof.

Thus, the encapsulated cells can be engineered to produce molecules having either inhibitory or enhancing activity depending on whether the target is an immune check-point with inhibitory (i.e., antagonistic) or enhancing (i.e., agonistic) capacity.

Synergy between cell-based immunization and CTLA-4/PD-1 blockade has been demonstrated in pre-clinical models. Preferably, local production of CTLA-4 is desirable.

The at least one biocompatible macrocapsule and/or the antigenic component may be frozen, stored, and thawed prior to use.

In any of the vaccine compositions described herein, the at least one biocompatible macrocapsule may also contain one or more of the following: i) a retrieval tube; ii) a retrieval hook secured to the retrieval tube, wherein the retrieval hook facilitates retrieval of at the at least one biocompatible macrocapsule after implantation; iii) a connector, wherein the connector secures the membrane of the at least one biocompatible macrocapsule to the retrieval tube; iv) a loading hub, wherein the loading hub facilitates the loading of the cells; and/or v) a transport tube, wherein the transport tube has a tube body and a tube cap.

Also provided are pharmaceutical compositions containing any of the vaccine compositions described and one or more physiologically acceptable carrier(s).

Also provided are kits containing the vaccine compositions and/or pharmaceutical compositions and instructions for use. For example, in such kits, the antigenic component may contain cells producing or releasing one or several antigens such as tumor cells that are optionally irradiated. Alternatively, the antigenic component may be obtained from an infectious agent (e.g., a virus, a bacterium, a parasitic pathogen, or a fungus).

In any of the kits described herein, the at least one biocompatible macrocapsules are sterilized (e.g., prior to use). Following sterilization, the at least one biocompatible macrocapsule can be individually packaged in sterile pouches for storage, transport, and/or delivery.

Also provided are uses of the vaccine compositions, pharmaceutical compositions, and/or kits described herein for therapeutic or preventative vaccination (e.g., cancer therapy or vaccination). By way of non-limiting example, the cancer may be selected from the group consisting of lung cancer, melanoma, breast cancer, colon cancer, pancreatic cancer, kidney cancer, acute leukemia, chronic leukemia, glioblastoma, low grade lymphoma, high grade lymphoma, multiple myeloma, sarcoma, bone cancer, brain tumor, stomach cancer, esophageal cancer, head and neck cancer, thyroid cancer, bladder cancer, prostate cancer, ovarian cancer, uterine cancer, chordoma, and cervical cancer. In some embodiments, the cancer is lung cancer; pancreatic carcinoma; ovarian carcinoma; or head and neck cancer.

In other embodiments, the therapeutic or preventative vaccination is infectious agent therapy or vaccination. For example, the infectious agent is selected from the group consisting of a virus (e.g., HIV, CMV, recurrent herpes infection, Hepatitis B, Epstein Bar virus, Hepatitis C, or human papilloma virus (HPV)), a bacteria (e.g., mycobacterial infection, *Helicobacter pylori*, or meningococcal infection), a parasite (e.g., malaria, toxoplasma, Pneumocystis, or echinococcosis), and a fungus (e.g., candida or aspergillus).

In any of these uses, the at least one biocompatible macrocapsule and the antigenic component are implanted and the at least one biocompatible macrocapsule is subsequently removed. For example, the at least one biocompatible macrocapsule and the antigenic component are administered sequentially under the skin in close proximity or contact. The antigenic load (i.e., the irradiated cancer cells or portion of the infectious agent) are not removed. Rather, they are degraded by the immune system.

The at least one biocompatible macrocapsule is implanted prior to the antigenic component.

The at least one biocompatible macrocapsule is implanted for less than 12 days; for between 4 and 10 days; or for between 5 and 7 days.

In any of these uses, the preventative or therapeutic vaccination involves multiple injections, for examples, multiple injections that occur at regular intervals. When the preventative or therapeutic vaccination is cancer therapy or vaccination, the regular intervals involve weekly injections for four weeks followed by two additional immunizations every two weeks. When the preventative or therapeutic vaccination is infectious agent therapy or vaccination, the regular intervals involve weekly injections for least two weeks. Preferably, the multiple injections are subcutaneous injections.

Also provided are methods for therapeutic or preventative vaccination by administering an effective amount of any of the vaccine compositions, pharmaceutical compositions, or kits described herein to a patient in need thereof. For example, the therapeutic or preventative vaccination is cancer therapy or vaccination. By way of non-limiting example, the cancer may be selected from the group consisting of lung cancer, melanoma, breast cancer, colon cancer, pancreatic cancer, kidney cancer, acute leukemia, chronic leukemia, glioblastoma, low grade lymphoma, high grade lymphoma, multiple myeloma, sarcoma, bone cancer, brain tumor, stomach cancer, esophageal cancer, head and neck cancer, thyroid cancer, bladder cancer, prostate cancer, ovarian cancer, uterine cancer, chordoma, and cervical cancer. In some embodiments, the cancer is lung cancer; pancreatic carcinoma; ovarian carcinoma; or head and neck cancer.

In other embodiments, the therapeutic or preventative vaccination is infectious agent therapy or vaccination. For example, the infectious agent is selected from the group consisting of a virus (e.g., HIV, CMV, recurrent herpes infection, Hepatitis B, Epstein Bar virus, Hepatitis C, or human papilloma virus (HPV)), a bacteria (e.g., mycobacterial infection, *Helicobacter pylori*, or meningococcal infection), a parasite (e.g., malaria, toxoplasma, Pneumocystis, or echinococcosis), and a fungus (e.g., candida or aspergillus).

In any of these methods, the at least one biocompatible macrocapsule and the antigenic component are implanted and the at least one biocompatible macrocapsule is subsequently removed. For example, the at least one biocompatible macrocapsule and the antigenic component are administered sequentially under the skin in close proximity or contact.

The at least one biocompatible macrocapsule is implanted prior to the antigenic component.

The at least one biocompatible macrocapsule is implanted for less than 12 days; for between 4 and 10 days; or for between 5 and 7 days.

In any of these methods, the preventative or therapeutic vaccination involves multiple injections, for examples, multiple injections that occur at regular intervals. When the preventative or therapeutic vaccination is cancer therapy or vaccination, the regular intervals involve weekly injections for four weeks followed by two additional immunizations every two weeks. When the preventative or therapeutic vaccination is infectious agent therapy or vaccination, the regular intervals involve weekly injections for at least two weeks. Preferably, the multiple injections are subcutaneous injections.

Finally, also provided are methods of preparing the at least one biocompatible macrocapsule used in any of the vaccine compositions described herein. For example, such methods may involve the steps of (a) culturing the allogeneic cells for at least two passages to insure that the cells secrete GM-CSF; (b) resusspending the cultured cells in a cell culture medium; (c) loading the cells into the at least one biocompatible macrocapsule (e.g., using sterile air pressure); and/or (d) cutting the retrieval tube in order to remove the loading hub. Such methods may also involve the further steps of sealing the cut end of the retrieval tube and/or washing and cryopreserving (e.g., using the vapor phase of liquid nitrogen) the at least one biocompatible macrocapsule.

Also provided are vaccine compositions, pharmaceutical compositions, and/or kits described herein for use in therapeutic or preventative vaccination.

For example, the therapeutic or preventative vaccination is cancer therapy or vaccination, optionally wherein the cancer is selected from the group consisting of lung cancer, melanoma, breast cancer, colon cancer, pancreatic cancer, kidney cancer, acute leukemia, glioblastoma, low grade lymphoma, high grade lymphoma, multiple myeloma, sarcoma, bone cancer, brain tumor, stomach cancer, esophageal cancer, head and neck cancer, thyroid cancer, bladder cancer, prostate cancer, ovarian cancer, uterine cancer, chordoma, and cervical cancer.

In other embodiments, the therapeutic or preventative vaccination is infection agent therapy or vaccination, optionally wherein the infection agent is selected from the group consisting of a virus, a bacteria, a parasite, and a fungus. By way of non-limiting example, the virus can be selected from the group consisting of HIV, CMV, recurrent herpes infection, Hepatitis B, Epstein Bar virus, Hepatitis C, and human papilloma virus (HPV), the bacterium is selected from the group consisting of mycobacterial infection, *Helicobacter pylori*, and meningococcal infection, the parasitic pathogen is selected from the group consisting of malaria, toxoplasma, Pneumocystis, and echinococcosis, or the fungus is selected from the group consisting of candida and aspergillus.

In any of the vaccine compositions, the pharmaceutical compositions, or the kits for use according described herein, the at least one biocompatible macrocapsule and the antigenic component are implanted and the at least one macrocapsule is subsequently removed, optionally the at least one biocompatible macrocapsule and the antigenic component are administered sequentially under the skin in close proximity or contact, or the at least one biocompatible macrocapsule is implanted prior to the antigenic component. For example, in the vaccine composition, the pharmaceutical composition or the kit for use, the at least one biocompatible macrocapsule is implanted for less than 12 days, for between 4 and 10 days, or for between 5 and 7 days.

In these vaccine compositions, the pharmaceutical compositions, or the kits for use, the preventative or therapeutic vaccination involves multiple injections, optionally wherein the multiple injections occur at regular intervals, optionally wherein the multiple injections are subcutaneous injections.

Also provided are vaccine compositions, the pharmaceutical compositions, or the kits for use described herein, wherein (i) when the preventative or therapeutic vaccination is cancer therapy or vaccination, the regular intervals are weekly injections for four weeks followed by two additional immunizations every two weeks, or (ii) when the preventative or therapeutic vaccination is infections agent therapy of vaccination, the regular intervals are weekly.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIGS. 1A-1E are a series of schematics of the biocompatible macrocapsules used in the vaccine compositions. FIG. 1A is a schematic of the entire biocompatible macrocapsule, which contain an internal coil (Detail J) upon which the allogeneic cells are distributed, a connector (Detail H), and a hook for retrieval (Detail I). FIG. 1B is a detailed schematic of the internal coil. FIG. 1C is a detailed schematic of the connector. FIG. 1D shows the suture used to hold the biocompatible macrocapsule in place following implantation. FIG. 1E is a detailed schematic view of the loading hub/transport tube.

FIG. 4 is a series of photographs showing the effect of MVX-ONCO-1 treatment on lung metastases.

FIGS. 7A-D show the results of the functional cell-based assay performed to determine the biological activity of the GM-CSF produced by the MVX-1 cell line.

DETAILED DESCRIPTION

Definitions

Figure 1A:
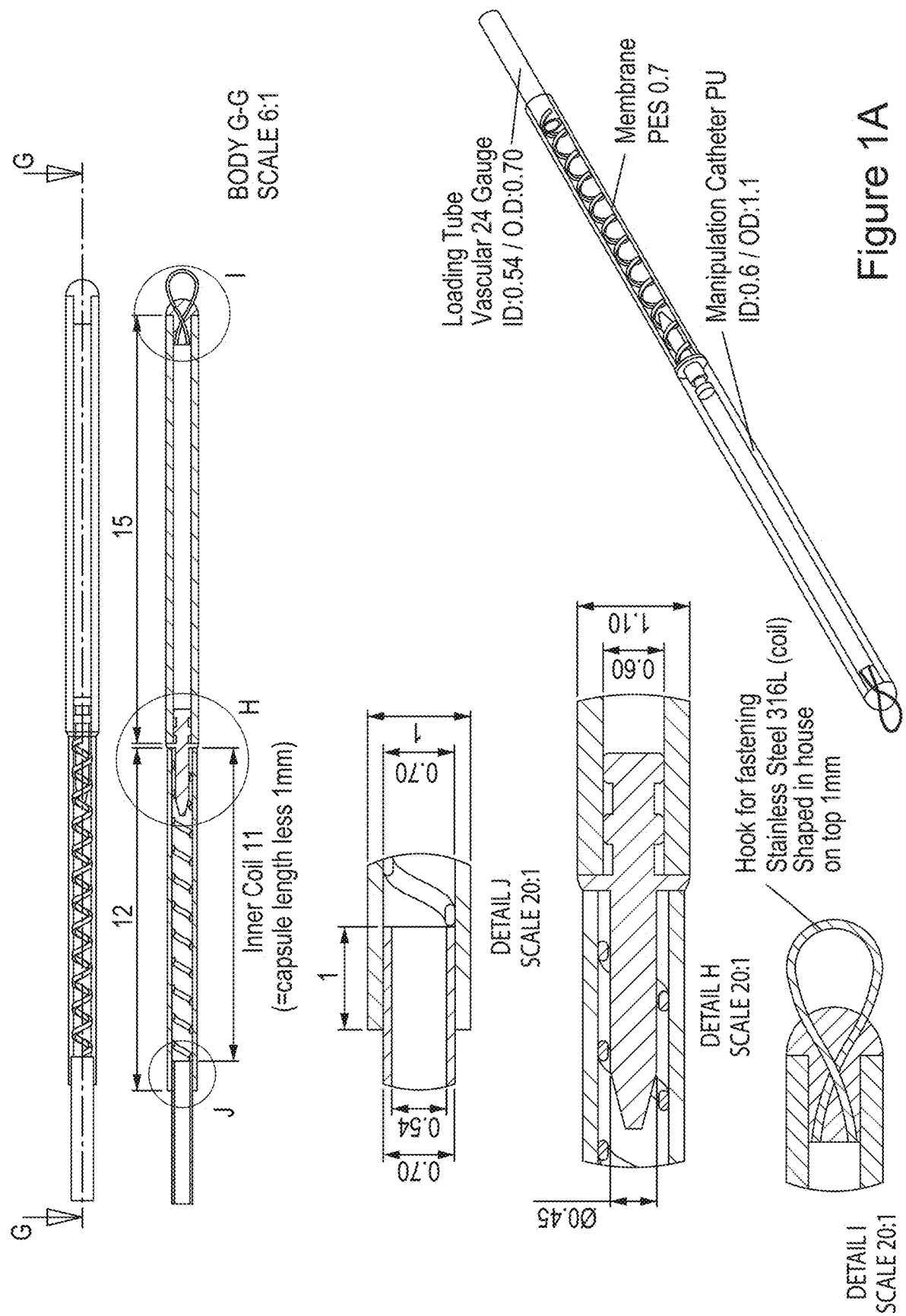

The terms "host", "subject", "patient" and the like are used interchangeably herein to refer to the subject receiving the immunization.

In the context of the present application, the following terms are defined in the following manner:

As used herein, the terms "immunomodulator" or "immunomodulatory agent" or the like refers to a compound or a composition that can enhance, amplify or decrease an immune response to an antigen or an immunogen. One non-limiting example of an immunomodulator is granulocyte macrophage-colony stimulating factor (GM-CSF). Those skilled in the art will recognize that any other suitable immunomodulator(s) known in the art can be used in the vaccine compositions described herein.

An "immunostimulatory agent" or an "immuno-activator" or the like is an immunomodulator that specifically enhances or amplifies the immune response to an antigen or an immunogen. The term "immunostimulatory agent" or "immuno-activator" is used synonymously herein with the term "adjuvant".

Cells are considered to be "immuno-isolated" if, when introduced into a host, they are physically protected against the immune response of the host, i.e., there is no significant acquired or natural immune response against any cell components, including cell-surface antigens, secreted proteins etc., provided there is no physical contact between the cells and the effectors of the immune system. Consequently, no significant antibody or cell-mediated immune response to the cell is seen in the host organism.

Immuno-isolated allogeneic cells are not attacked or destroyed by the immune response of the host, because they are undetectable by the immune system, which prevents any immune response against them and because they are physically protected against any immune response.

As used herein, the terms "encapsulation" or "encapsulated" or the like refer to a particular means of immuno-isolating cells in a biocompatible device (i.e., a macrocapsule or encapsulated cell therapy (ECT) device) containing a capsule of material, for example plastic, which is non-immunogenic for the host organism. The action of encasing a cell or population of cells in a barrier device such as a biocompatible macrocapsule is known as macroencapsulation. The terms "capsule", "device", "macrocapsule" and the like are used interchangeably here in to refer to the macrocapsules that make up one of the components of the vaccine compositions described herein.

Vaccine Compositions

The vaccine compositions described herein contain two components: an antigenic component and at least one retrievable biocompatible macrocapsule containing allogeneic cells that secrete an immunomodulator (i.e., GM-CSF) for use in therapy and/or preventative vaccination. Preferably, the encapsulated cells are engineered to produce the immunomodulator, although the use of cells and cell-lines which naturally produce the immunomodulator is also encompassed.

Also provided are pharmaceutical compositions and kits which can be used in this context. Any of the vaccine compositions, pharmaceutical compositions, or kits described herein are suitable for use in therapeutic and/or preventative vaccination. Likewise, any of the vaccine compositions, pharmaceutical compositions, or kits described herein can be used in methods of therapeutic and/or preventative vaccination.

For example, the therapeutic or preventative vaccination may be tumor or cancer therapeutic or preventative vaccination or therapeutic or preventative vaccination against one or more infectious agents.

The immunomodulatory agent produced can be a protein synthesized by the macroencapsulated allogeneic cells, but it can also be for example a cell-component such as a lipid, or an exogenous molecule further transformed by the cell, for example antigens processed by antigen-presenting cells or metabolites. In one embodiment, the immunomodulatory agent is huGM-CSF. Because in cell-based cancer immunization protocols, antigens are frequently too weak to trigger a significant immune response and some molecules involved in this response are known to enhance or amplify it, the immunomodulatory agent is preferably an immunostimulatory agent that may function by attracting antigen-presenting cells (e.g., dendritic cells) and that may also stimulate the activities of CD4 or CD8 T-cells.

Particularly potent immunostimulatory agents belong to the cytokine family. Suitable cytokines include, but are not limited to, GM-CSF (Granulocyte and Granulocyte-Macrophage Stimulating Factor), IL-3, IL-4, IL-9, IL-1, IL-2, IL-7 (interleukin), transmembrane receptors of IFNα, SCF (Stem Cell Factor) soluble or membranous, FL (Flt3 Ligand), G-CSF, as well as any combinations thereof. Preferred immunostimulatory agents are GM-CSF (e.g., human GM-CSF) and FL.

In the context of cancer therapy, GM-CSF is particularly recommended as immunostimulatory agent because it has been identified as the most potent cytokine for activating systemic antitumor immunity. (See Dranoff et al, 1993, Proc Natl Acad Sci USA, 90(8):3539-43). However, GM-CSF is also effective as an immunostimulatory agent in infectious agent vaccination and therapy.

In order to induce an adequate immune response, it can be very advantageous to combine several immunomodulatory agents, which may stimulate different pathways. For example, one preferred combination is GM-CSF and FL. However, any other combinations of two or more immunomodulatory agents can also be used. Determination of the suitable combinations is within the routine level of skill in the art.

Immuno-isolation overcomes the significant disadvantages associated with the use of HLA-negative cells such as the K-562 cell line. Because the encapsulated cells are entirely protected against the immune system, they are not destroyed by innate or cellular immunity, in contrast to non-encapsulated K-562 cells, which are involved in innate immunity rejection. The capacity of macroencapsulated cells to survive, secrete protein for a prolonged period of time, and allow multiple immunizations is directly linked to the physical barrier of the macrocapsule. Moreover, the amount and duration of GM-CSF release into the patient following capsule implantation is not likely to differ from one individual to another depending on his or her innate immunity or immunosuppression. In contrast, when non-immuno-isolated cells (i.e., GM-CSF secreting K-562 cells) are used, the stability of GM-CSF release is likely to vary significantly both in any given patient between the first and subsequent immunizations and also from one patient to another.

A preferred way to immuno-isolate cells is to provide a physical barrier "hiding" them from the general immune system, which can be achieved by a barrier device such as a biocompatible macrocapsule having a core containing the cells and an internal coil with the cells distributed on it surrounded by a semipermeable membrane.

Immuno-isolation if the immunomodulator secreting cells overcomes the significant disadvantages associated with the implantation of free cells, which generally requires immunosuppressing drugs in order to protect them against the immune system of the host. By mechanically blocking immune attacks, the use of barrier devices such as macrocapsules obviates the need for immunosuppressive therapy. Moreover, if desired, the cells can be retrieved readily after a define period of time, which allows for a switchable release of the immunomodulatory agent. By retrieving the implanted device, the release of the agent is stopped, which prevents unwanted presence of a molecule after the end of the immunization process.

Barrier devices such as the biocompatible macrocapsules used in the vaccine compositions described herein separate living cells from the immune system of the host by a synthetic, selectively permeable, non-immunogenic membrane. The use of a semi-permeable membrane allows free exchange of nutriments, proteins, oxygen and biotherapeutic substances between exterior and interior. Small molecules (e.g., molecules necessary for the survival of the cells) can transit via pores in the membrane of the macrocapsule, whereas high-molecular-weight substances such as immunocytes or antibodies are excluded. The membrane also excludes inflammatory cells and thereby protects the encapsulated cells from tissue rejection.

Conversely, immunomodulatory agents produced by the cells can be delivered through the pores into the external medium. The diameter of the pores is preferably chosen in a range such that small molecules or proteins and immunomodulators are allowed to cross the barrier and that bigger ones like immunoglobulins are not, in order for the device to retain its immuno-protective property.

The capsules may have various shapes and sizes. Specifically, the capsule can be any configuration appropriate for maintaining biological activity and providing access for delivery of the product or function, including for example, cylindrical, rectangular, disk-shaped, patch-shaped, ovoid, stellate, or spherical. If the capsule is to be retrieved after it is implanted, configurations which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired. In one embodiment, the macrocapsule is cylindrical in shape.

The semi-permeable membrane of the devices described herein is made from a permselective, immunoprotective membrane or from an ultrafiltration membrane or a microfiltration membrane. Those skilled in the art will recognize that a semi-permeable membrane typically has a median pore size of about 100 nm. In still other embodiments, the semi-permeable membrane may be made from a non-porous membrane material (e.g., a hydrogel or a polyurethane).

Various polymers and polymer blends can be used to manufacture the surrounding semipermeable membrane, including polysulfones (including polyethersulfones (PES)), polyacrylates (including acrylic copolymers), polyvinylidenes, polyvinyl chloride copolymers, polyurethanes (including thermoplastic polyurethane), polystyrenes, polyamides, cellulose acetates, cellulose nitrates, polyphosphazenes, polyacrylonitriles, poly(acrylonitrile/covinyl chloride), as well as derivatives, copolymers and mixtures thereof. By way of non-limiting example, polymers for the capsule are thermoplastic polyethersulfone (PES) hollow fibers (OD:720 μm; ID:524 μm, molecular weight cut-offs: 32 and 80 kDa; Akzo Nobel Faster AG, Wupperthal, Germany) and AN-69 polymer (acrylonitrile and sodium metallysulphonate anionic copolymer, Hospal R&D Int, Meyzieu, France).

In any of the macrocapsules described herein, the nominal molecule weight cutoff (MWCO) of the semi-permeable membrane is 500 kD. In some embodiments, the MWCO is approximately 280 kD.

Several different membrane thicknesses with several pore dimensions were tested (e.g., PES5, UltraPES 0.8, and UltraPES 0.7). Ultimately, UltraPES0.7 (Membrana GmbH, Wuppertal, Germany) was selected for use in the clinical trial. Similarly, various capsule lengths were also tested and 12 mm was selected as the best size for implantation, handling, manufacture, and cell loading procedures.

Preferably, the semi-permeable membrane is between about 90-120 um thick. Any of the devices described herein can be configured as a cylinder, hollow fiber, or a flat sheet. The length of the device can be between about 4 mm-15 mm. In some embodiments, the device has an internal diameter of between about 0.9 mm 1-1.2 mm. The ends of the device can be sealed using a connector or methyl methacrylate.

In some embodiments, macroencapsulation makes use of preformed macrocapsules that are formed from a membrane designed to be implanted subcutaneously. These macrocapsules also contain a retrieval tube that is situated between the dermis and subcutaneous layer. In some embodiments, the retrieval tube is made of a medical grade polymer (including thermoplastic polyurethane, Low and High Density Polyethylene, PEEK, Polycarbonate urethane and/or Thermoplastic Elastomers).

At the end proximal to the physician (i.e., distal to the membrane) the retrieval tube has a tether hook (also referred to as a retrieval hook), which can be used to facilitate the retrieval of capsule following implantation. Preferably, the retrieval hook has an eyelet at one end and at the other end has two legs to facilitate attachment inside of the retrieval tube. By way of non-limiting example, the retrieval hook is made of a medical grade stainless steel (i.e., the stainless steel alloys 316LVM, 316L, 302 and/or 304). The retrieval hook can be secured using any suitable methods known in the art. By way of non-limiting example, it can be secured using an ultraviolet (UV) light curable glue and/or a suture can be placed through the eyelet in the retrieval hook, which remains outside the skin following macrocapsule implantation.

A connector can be used to facilitate the connection of the macrocapsule's membrane to the retrieval tube. By way of non-limiting example, a stainless steel connector can be glued to the membrane. In some embodiments, the end of the connector that is inserted into the membrane has a conical shaped end (e.g., a truncated conical shape).

The macrocapsules contain an internal coil that is made from a medical grade metal such as, for example, aluminum or titanium, which can be inserted onto the truncated conical end of the connector. This internal coil ensures a good ordering of the cells inside the capsule, specifically a homogenous distribution, and prevents agglutination at the walls. The internal coil may also prevent cells from aggregating and improving cellular distribution within the device. (See PCT Publication No. WO 96/02646).

Figure 1B:
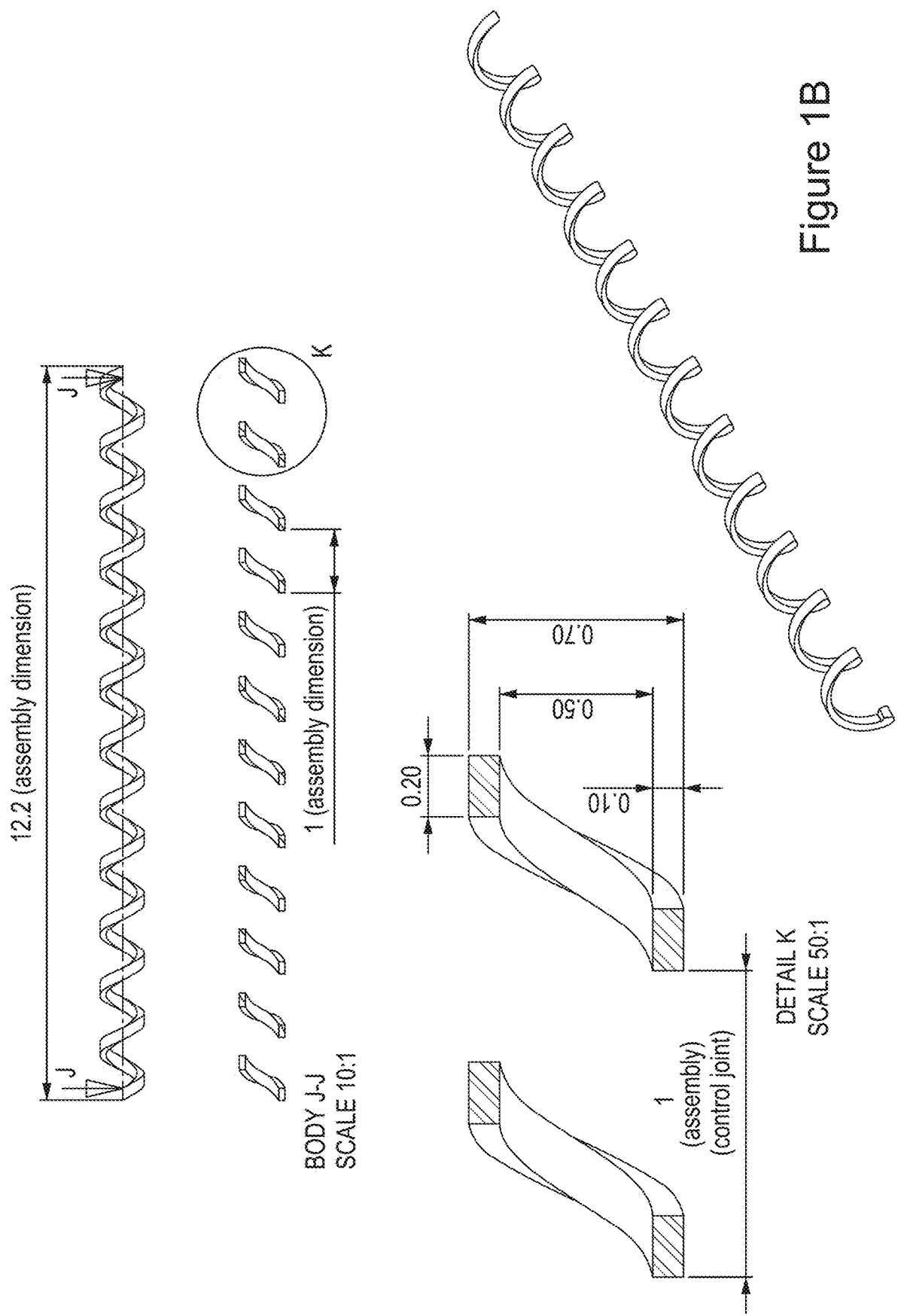
Figure 1C:
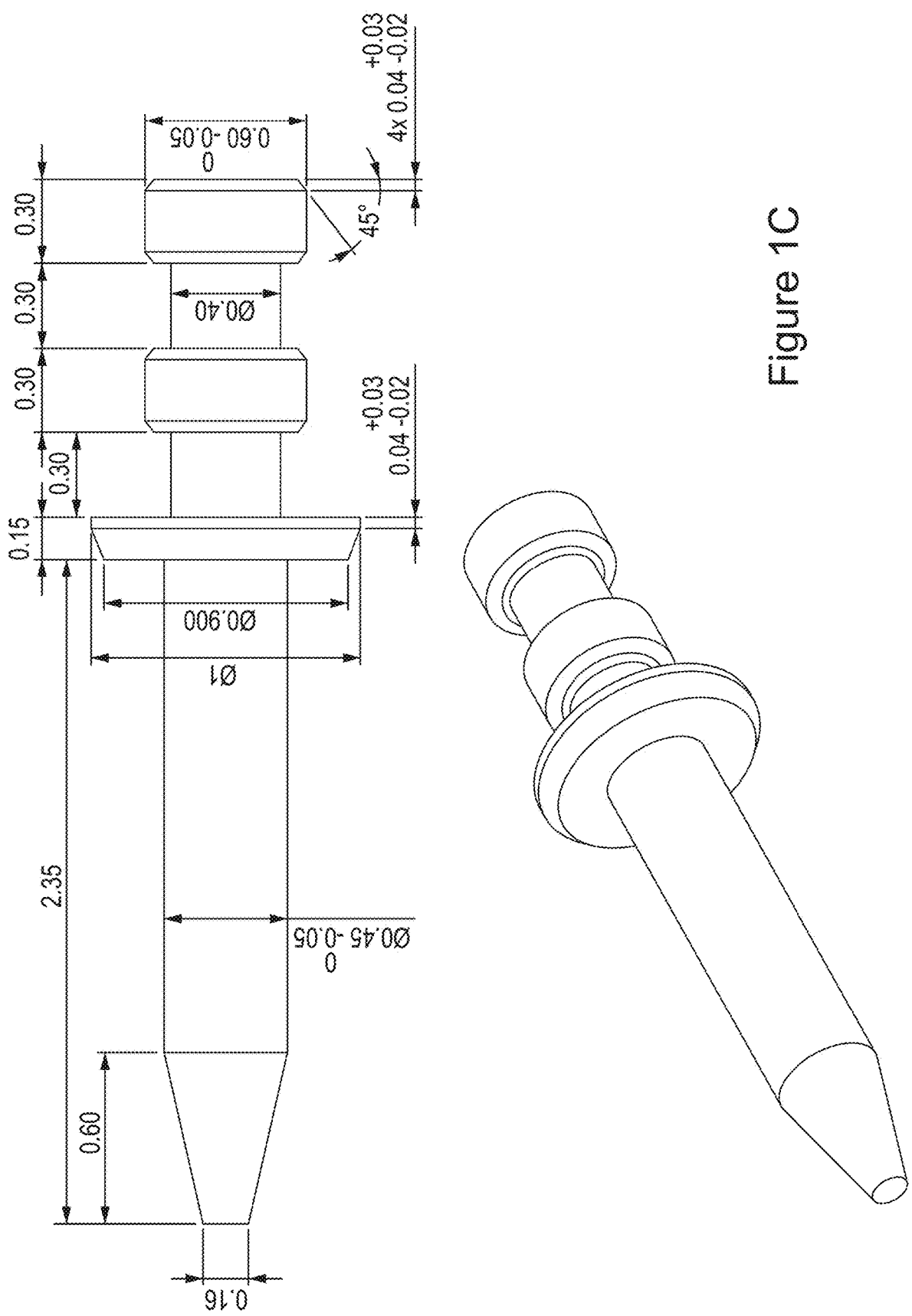
Figure 1E:
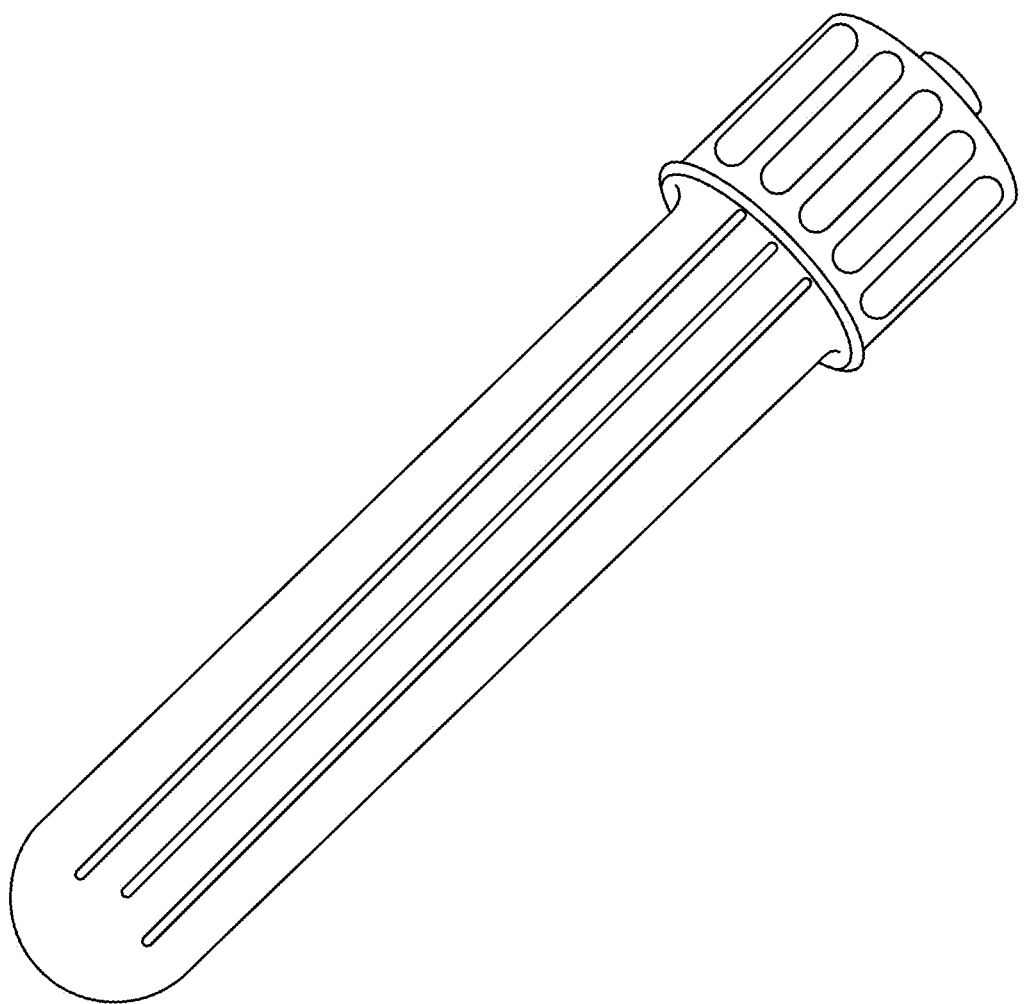
Figure 2:
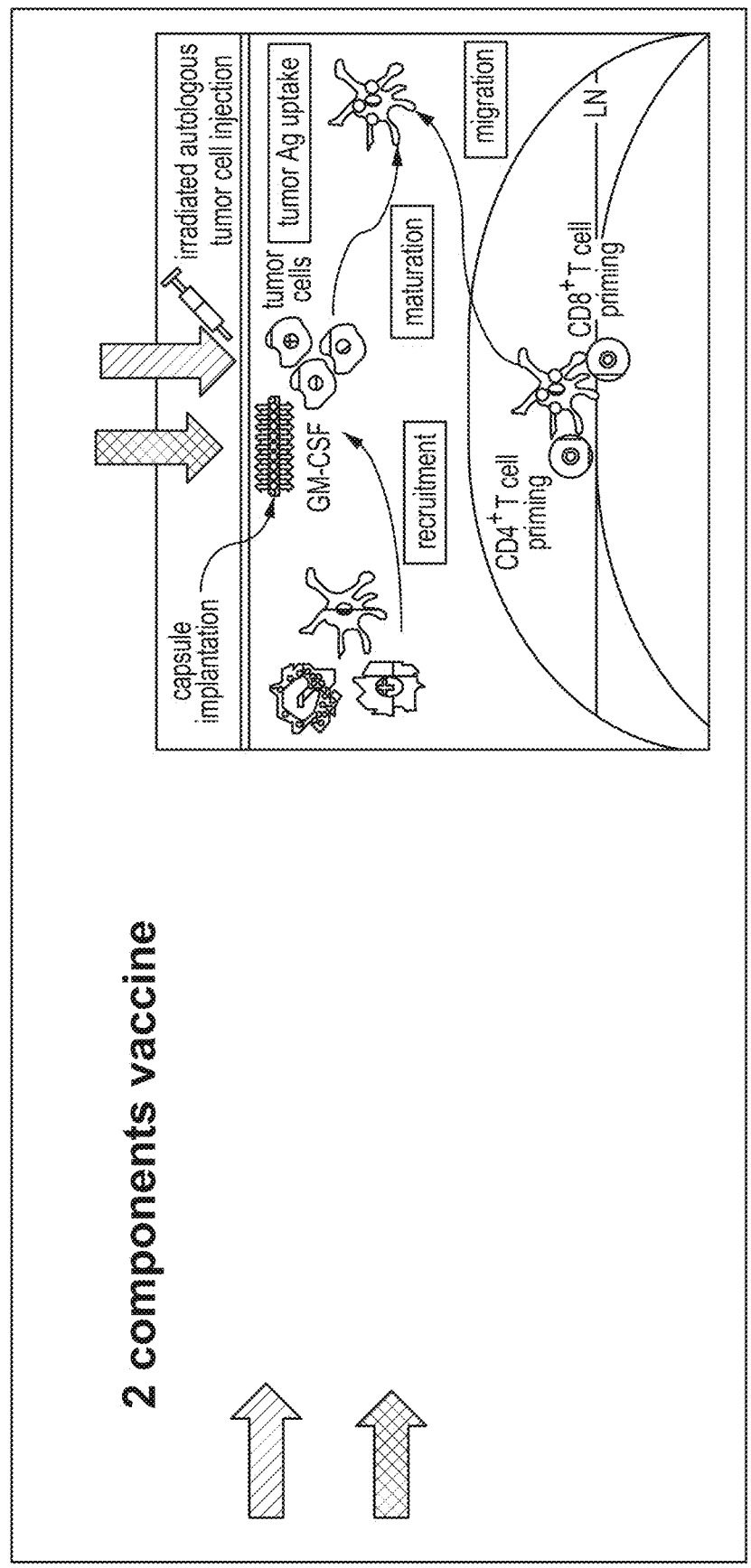
FIG. 2 is a schematic showing the two component cancer vaccine strategy described herein (Onco-Maxi-Vax).
Figure 3:
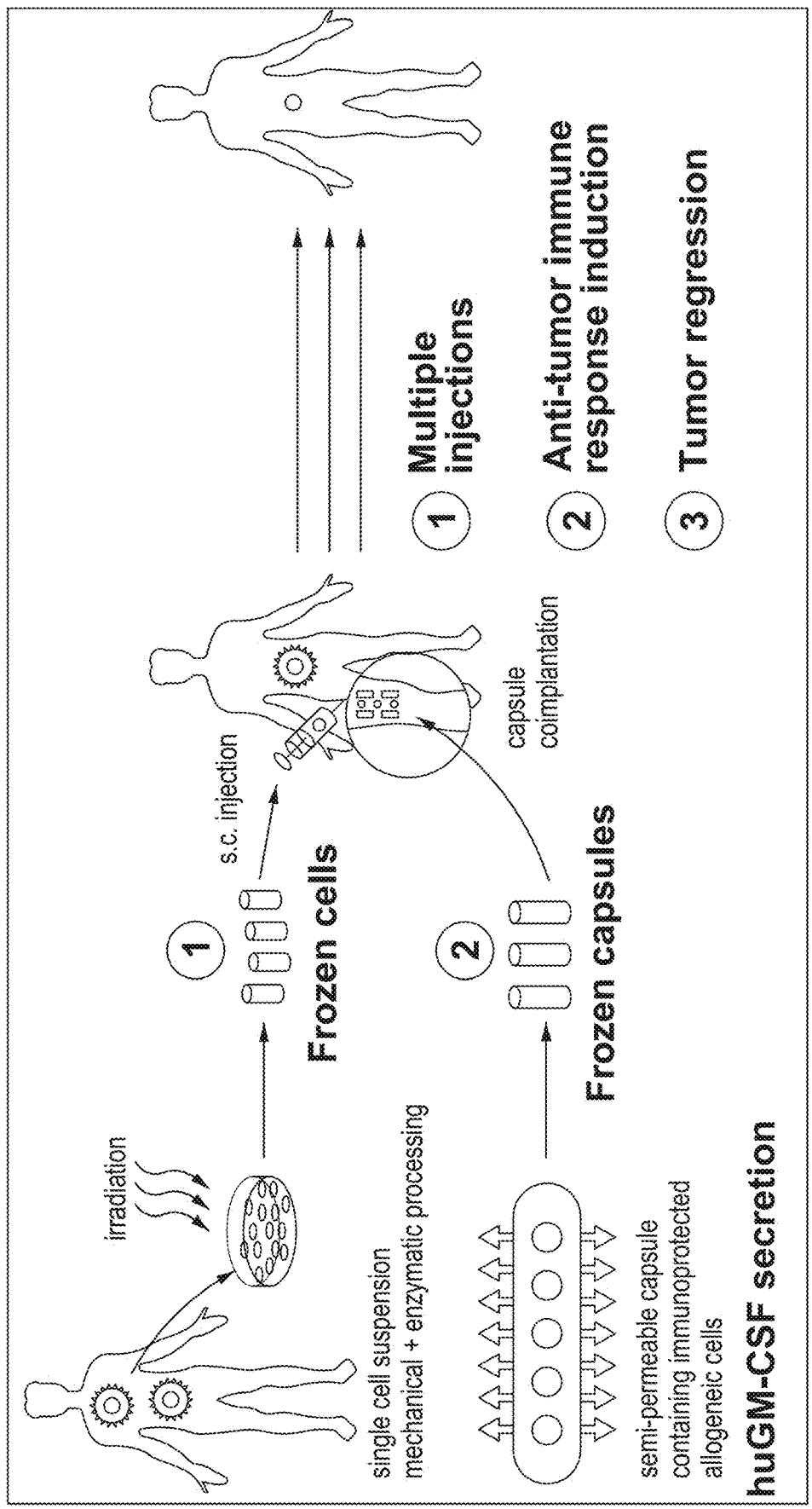
FIG. 3 is a schematic showing the cancer therapeutic vaccination strategy described herein. In this protocol, a single cell suspension of autologous tumor cells are processed, irradiated and frozen prior to subcutaneous injection. Likewise, biocompatible macrocapsules containing immuno-isolated GM-CSF-secreting allogeneic cells are frozen prior to implantation. At the time of treatment, the irradiated autologous tumor cells are subcutaneously injected, and the macrocapsules are implanted in a similar location. The subcutaneously implanted capsules are removed after 7 days, while the irradiated tumor cells are destroyed by the patient's immune system. This protocol involves multiple injections and results in induction of anti-tumor immune response and potential tumor regression in treated patients.

Suitable internal coils will have a defined number of spires per centimeter. For example, the coil can be formed from raw materials (Hefaeus Materials) that are stretched to form a reinforced spring having a specific distance between spires (e.g., 1 mm±0.1 mm). (See FIG. 1B).

Once a suitable internal coil is formed, the membrane is slid over the reinforcement spring (i.e., the internal coil) and sealed to the retrieval tube using a UV curable glue. In one embodiment, the membrane is placed approximately 2 mm into the polyurethane core and glued just before the truncated conical end of the connector. In other embodiments, the entire retrieval tube is filled with glue in order to secure the membrane.

Empty macrocapsules can be loaded with an internal coil, for example, using a loading hub (e.g., BD Vasculon™ or BD Insyte-W™0.9 mm×25 mm) that has been ethylene oxide (EO) sterilized. This loading hub is secured to the membrane, for example, using a UV photocurable glue. In some embodiments, the loading hub has a truncated conical end that friction fits into the membrane end of the connector.

A transport tube can be modified from a Falcon 14 mL tube by drilling one or more holes in a tube body and in the tool cap. Those skilled in the art will recognize that these holes should be aligned with the membrane when inserted to insure good EO sterilization. A luer lock can be inserted and friction fitted into the cap. The loading hub can then be matingly engaged into the luer lock cap. The completed transport tube is then sterilized and returned into sterile pouches that are individually packaged.

The macrocapsules can have various sizes ranging from few micrometers to three to four centimeters. Depending on the size of the capsule and the size of the cells, as many as 200,000 cells can be loaded into a 1 cm device. In some embodiments, the device is cylindrical in shape and is about 12 mm long. Those skilled in the art will be able to determine the optimal configuration (i.e., shape, size, length, number of cells, etc.) for the macrocapsules used in the vaccine compositions described herein without any undue experimentation.

Suitable allogeneic cells for use in the macrocapsules described herein can be obtained from a working cell bank, which contains $5 \times 10^6$ cells/aliquot stored in liquid gas. These cells are thawed prior to use and cultured for 2-3 passages in Complete medium RPMI 1640 with 10% FBS, penicillin/streptomycin and G418 (a selective antibiotic) to ensure that cells secrete GMCSF. Approximately 800,000 cells are then resuspended in 30 μl of Complete medium, and the entire 30 μl is then loaded into each capsule using sterile air pressure. The retrieval tube is then cut to remove the loading hub, and the end of the retrieval tube is sealed with UV glue.

The capsule is then washed in Complete medium (aseptic) and incubated in 6 well dish with aseptic Complete medium (approximately 3-5 ml of medium).

Macrocapsules may contain between 1×10$^5$ allogeneic cells and 1×10$^6$ allogeneic cells (e.g., 8×10$^5$ cells) per capsule. These cells are contained within the core of the macrocapsules, are distributed on the internal coil within the macrocapsules, and are surrounded by the semipermeable membrane.

Prior to culture, a safety/quality control (QC) step can be formed. The purpose of this safety QC step is to assess the microbiological, mycoplasma, and LAL/endotoxin "status" of the cells. Microbiological and mycoplasma assessment is performed by sampling the supernatant and culturing it over selective agar. LAL/Endotoxins are also quantified in a sample of the supernatant, but via a reaction with bacterial endotoxin and/or lipopolysacharride.

Following a 7 day culture, the supernatant is measured for GM-CSF secretion. Preferably, the devices secrete at least 20 ng/capsule/day. Typically, between about 50-150 ng/capsule/day is secreted. Thus, the claimed macrocapsules are suitable for sustained delivery of low doses of the immunostimulatory agent (i.e., GM-CSF).

Several concentrations of cells within the macrocapsules were tested (e.g., 5, 8, 10, and 15×10$^5$ cells). 8×10$^5$ cells was the concentration selected because it offers the best long term stability for long-term release with minimal variability.

Once manufactured, the macrocapsule devices can be cryopreserved prior to use using any methods known in the art. For example, in some embodiments, cryopreservation is performed in the vapor phase of liquid nitrogen.

The immuno-isolated allogeneic cells used in the vaccine compositions described herein are living and preferably provide the chosen immunomodulatory agent on a long-term basis (e.g., for at least 2, 3, 4, 5, 6, 7, 8, 9, 10, 11, 12, 13, 14, 15, 16, 17, 18, 19, 20, or more days). In one embodiment, the immuno-isolated cells secrete the immunomodulatory agent for a period of at least 7 days.

The immuno-isolated allogeneic cells may either naturally produce the immunomodulatory agent or they may be genetically engineered to express the immunomodulatory agent. By genetically engineering a cell that normally does not produce the immunomodulatory agent, the vaccine compositions are not limited to those cells naturally producing it. Suitable immunomodulatory agents are not limited to those naturally occurring, as it is known that mutated proteins sometimes exert improved activities. Thus, the immunomodulatory agent may be a modified version of the protein instead of the wild-type one. In some cases, the cells are genetically engineered to secrete the soluble version of a membranous protein, in order to achieve its secretion.

Moreover, by genetically modifying cells, it is also possible to control the expression level of the immunomodulatory agent. One particularly attractive situation is the overexpression of the agent by cloning its sequence under the control of a promoter known to be very strong in the used cell. In this way, the modified cells become engineered factories producing high levels of immunomodulatory agent. The promoter can be chosen according to its activity in order to have a controlled level of immunomodulator expression. In another embodiment, cells may be used which naturally contain the gene for the immunomodulatory agent, wherein the gene is transcriptionally silent in that particular cell. In this situation, transcription can be activated by insertion of appropriate regulatory sequences, for example by homologous recombination. Inducible regulatory sequences which respond to specific stimuli such as substances, light, etc. may also be used.

In some embodiments, immunomodulatory agent-secreting cells can secrete more than 10 ng/10$^6$ cells/24 hr of immunomodulatory agent (e.g., GM-CSF). For example, the cells may secrete a quantity of immunomodulatory agent equal or superior to 100 ng/10$^6$ cells/24 hr, or more than 500 ng/10$^6$ cells/24 hr. Allogeneic cells that secrete more than 10×10$^{-15}$ g of immunomodulatory agent per 24 hr or more than 100×10$^{-15}$ g/24 hr of immunomodulatory agent can be used. For example, cells that secrete between 80 and 960× 10$^{-15}$ g/24 hr or more than 500×10$^{-15}$ g/24 hr of immunomodulatory agent can be used. The devices described herein can secrete at least 20 ng/capsule per day. For example, the devices can secrete between 50-150 ng/capsule/day (e.g., 50, 55, 60, 65, 70, 75, 80, 85, 90, 95, 100, 105, 110, 115, 120, 125, 130, 135, 140, 145, or 150 ng/capsule/day).

If needed, several capsules (e.g., 2, 3, 4, 5, 6, 7, 8, 9, 10, or more) may be implanted simultaneously in order to achieve the desired secretion level.

Any method of genetic modification known in the art can be used to genetically modify the immuno-isolated allogeneic cells. For example, engineered plasmids introduced by transfection and viruses introduced by infection can be used. Retroviruses can be used because they can be engineered to introduce a gene coding for the immunomodulatory agent into the genome of host cell.

Suitable allogeneic cells are not limited to cells naturally producing an immunomodulatory agent of interest. Rather, a variety of cells can be used. Preferably, the cells are easy to transduce or transfect, to culture, and to propagate. In any of the vaccine compositions described herein, it is not necessary to use tumor cells as the bystander immunomodulator producer. Those skilled in the art will be able to utilize different cell types such as, for example, immortalized non-tumoral fibroblasts, myoblasts, tumor cells, endothelial cells, fibroblasts, or cells of hematopoietic origin. Determination of the appropriate cell type is within the routine level of skill in the art.

For manufacturing reasons, non-adherent cells (excluding fibroblasts or epithelial cells), which can easily be stored frozen can be used. For safety reasons, only biosafety level 1 cells were tested. Five different cell lines were tested for their ability to undergo encapsulation: CCL243, CCL246, CCL246.1, TIB202, and CRL1582. CCL243 (a cell of hematopoietic origin) was finally selected and subsequently genetically modified to express huGM-CSF. MVX-1 is the cell line obtained from single cell cloning of the genetically modified CCL243 cell line. Capsules loaded with MVX-1 cells were selected for their ability to efficiently be frozen for long term storage up to 18 months (i.e., up to 1, 2, 3, 4, 5, 6, 7, 8, 9, 10, 11, 12, 13, 14, 15, 16, 17, or 18 months). The GM-CSF produced by the MVX-1 cell line has been deemed equivalent to commercially available GM-CSF in a functional cell-based assay. (See Example 6, infra).

In some embodiments, the allogeneic cells are immortal or immortalized cell lines, which can be genetically modified once and used for all compositions and methods described herein. Because the cells are immuno-isolated within biocompatible macrocapsules, they are not endangered by the immune system of the host, and the use of immortalized cells does not endanger the other cells in their vicinity.

Importantly, because the cells are macroencapsulated, allogeneic or heterologous cells can be used. Thus, it is not necessary to utilize autologous cells. The cells used in the vaccine compositions are preferably human cells.

Those skilled in the art will recognize that the immuno-isolation of the cells within biocompatible macrocapsules is advantageous because the source of immunomodulatory agent is not limited to a unique individual.

Because the allogeneic cells within the macrocapsules are living, the immunomodulator is continuously produced, for at least several (e.g., at least 2, 3, 4, 5, 6, 7, 8, 9, 10, 11, 12, 13, 14, 15, 16, 17, 18, 19, 20, or more) days.

Implantation

Cryopreserved capsules are thawed and cultured for at least 7 days prior to implantation. For days 1-4, culture occurs in Complete medium, while for days 5-7, culture occurs in a reduced medium lacking penicillin and streptomycin. Capsules are then assayed for GM-CSF secretion on day 7. Before implantation, the capsule is maintained in an incubator and placed into a Falcon 15 mL tube with the reduced medium and transported to the operating or implantation room.

Determination of the appropriate implantation protocol is within the routine level of skill in the art.

By way of non-limiting example, patients can be given a local anesthetic prior to implantation. Doctors can attach a retrieval suture loop (e.g., a polyamide suture loop) to the retrieval loop and use a 14 gauge needle to introduce the catheter (e.g., B Braun 14 gauge Vasofit catheter). The capsule is then inserted into the catheter and an inserter tool is used to move the capsule down the barrel of the catheter. The catheter is then removed, but the inserter tool is used to ensure that the capsule remains in place subcutaneously during removal.

The immuno-isolated allogeneic cells are implanted for a few days, for example, less than 12 days (e.g., less than 11, 10, 9, 8, 7, 6, 5, 4, 3, 2, or 1 day), for example between 4 and 10 days, for example between 5 to 7 days. Implantation of immuno-isolated allogeneic cells for such a short period will not lead to marked fibrosis induced by the release of the immunomodulatory agent. Moreover, inflammation at the vaccination site and/or around the macrocapsule, will not induce a decrease of cell viability within the capsule, and, therefore, it will not prevent the production and release of the immunomodulatory agent in that time frame.

The macrocapsules can be irradiated, for example by X-Rays, before implantation. Irradiation ensures that, even if disruption of the capsule occurs, enclosed cells are not capable of propagation. Moreover, irradiation ensures that the secretion of the immunomodulatory agent will stop after around 10 days, due to irradiation-induced cell death. This, in turn, may be advantageous, if the secreted immunomodulatory agent generates a violent inflammatory response. Specifically, subcutaneous implantation of macroencapsulated GM-CSF-secreting immuno-isolated allogeneic cells could induce cutaneous necrosis if implanted for a period exceeding 15 days to 1 month. Irradiation of the capsule or cells before implantation does not prevent subsequent retrieval of the capsule.

In certain embodiments, two capsules are implanted into a patient, approximately 5-15 mm apart (i.e., 5, 6, 7, 8, 9, 10, 11, 12, 13, 14, or 15 mm apart). Importantly, due to the inherent mechanism of action of the therapy methods described herein, implantation should not occur in proximity to the tumor. Selection of the appropriate location and separation distance for the capsules is within the routine level of skill in the art.

When the capsules are implanted in the patient, they can be secured with a patch such as steristrips to prevent them from moving from the implantation site. The implanted capsules with the suture, which sticks out of the patient's skin, is covered with a transparent patch to monitor the vaccination site.

MVX-ONCO-1

Any of the vaccine compositions, pharmaceutical compositions, or kits described herein can be used in the context of cancer therapy or in a method of treating cancer. This product has been designated "MVX-ONCO-1", which is a therapeutic product (therapeutic vaccine) made of two components that are physically in close proximity during the immunization.

One component of the MVX-ONCO-1 system is the source of tumor antigens (i.e., the antigenic component), which is made of irradiated autologous cells harvested from the patient to be treated and is specific for each patient. Preferably, patient tissue is taken from non-irradiated patients. Prior to use, a pathologist can confirm that the excised tumor or cancer cells are excised. For solid tumors, approximately 5-10 g (e.g., 5, 6, 7, 8, 9, or 10 g) of tissue is excised.

In one embodiment, one component includes between about $1\times10^6$ and about $1\times10^7$ autologous tumor cells (e.g., about $4\times10^6$ autologous tumor cells). In order to ensure maximal antigen exposure the source of antigen is made of each patient's own tumor cells, which can be obtained from a biopsy, surgery, or tap.

For pleural effusion (or other liquid samples), approximately 1 liter is collected, and the liquid samples are centrifuged, washed in buffer (i.e., Hank's Balanced Salt Solution), and the cells are counted.

For solid samples, GMP grade collagenase IV can be used to digest the tissue. Mechanical digestion with a scalpel can alternatively or additionally be used in order to cut the tissue into small pieces. The resulting tissue fragments are then placed into a plastic bag and are further mechanically pressure digested using a laboratory paddle or blade blender.

Next, the digested tissue fragments are dispensed into 50 mL Falcon tubes and centrifuged. The supernatant is discarded and the pellet is washed with a buffer that lacks $Ca^{2+}$ and $Mg^{2+}$ to inactivate collagenase, which requires the presence of a divalent cation for activity. The pellet is then resuspended and filtered through a 70 µm mesh, which allows single cells to pass through. Then, the cells are pelleted again and the cells are counted. Those skilled in the art will recognize that a Trypan blue test for cell viability can also be performed.

Cells obtained from either a liquid or a solid tumor sample are digested in order to obtain a cell-suspension and then irradiated at 10000 Rad (i.e., 15-150 gray (Gy)) prior to storage in aliquots in liquid nitrogen. Irradiation is performed as a safety measure in order to prevent any growth of tumor cells that are being re-injected to the patients. Lethally irradiated tumor cells can be frozen for long term storage up to 12 months (i.e., up to 1, 2, 3, 4, 5, 6, 7, 8, 9, 10, 11, or 12 months).

When the vaccinating process is used in the field of cancer, the antigenic component is a whole tumor cell. Because some antigens are present on many tumors from the same lineage, the tumor cells may be allogeneic ones. However, the tumor cells are autologous with respect to the patient.

The irradiated autologous cells can be aliquoted into a suitable dose for single vaccination. Preferably, the supernatant is reserved for mycobiologic, mycoplasma, and/or endotoxin screening. Individual aliquots can then be cryopreserved in dimethyl sulfoxide (DMSO). Prior to implantation, DMSO can be washed away, and a suspension in a small volume can be prepared. By way of non-limiting example, a solution of $4\times10^6$ cells in 500 µl of HBSS can be prepared.

The other component of MVX-ONCO-1, which is common to all patients, is the immunomodulator provider. This component contains at least one retrievable biocompatible macrocapsule containing immuno-isolated allogeneic cells that secrete the immunomodulator. In one embodiment, the macrocapsules contain between about $1\times10^5$ and about $1\times10^6$ immuno-isolated allogeneic cells (e.g., about $8\times10^5$ cells) that secrete at least 20 ng/24 hour of GM-CSF (e.g., 20-500 ng/24 hour) In various embodiments, the immuno-isolated allogeneic cells secrete 20, 30, 40, 50, 60 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or more ng/24 hour of GM-CSF).

In the MVX-ONCO-1 vaccine composition, the encapsulated cells are genetically engineered to secrete immunostimulatory molecules (for example, GM-CSF) and function as an immuno-isolated bio-reactor that produces and secretes strong immuno-stimulatory signals at the site of vaccination. Currently, GM-CSF is the most potent immunostimulatory molecule for generating anti-tumor immune responses. Thus, the encapsulated cells can be genetically engineered to secrete GM-CSF only. However, depending on synergistic studies, other immunomodulatory molecules can be added to or substituted for GM-CSF without difficulty. For example, other cytokines such as IL-12, IL-15, IL-4, Interferon gamma, chemokines or dendritic growth factors, IL-3, IL-9, IL-1, IL-2, IL-7, transmembrane receptors of IFNα, Stem Cell Factor (SCF) soluble or membranous, FL (Flt3 Ligand), G-CSF, TLR7 agonists, TIM-3, GITR, TIM-3 GITR, LAG-3, Vista, BTLA, ICOS, OX40, CD40, CD137 (also known as 41BB), CD27, and any combination(s) thereof can be added to or substituted for GM-CSF.

The two components of the cancer vaccine compositions described herein are placed under the patient's skin in close proximity or in contact. For example, the solution containing the irradiated autologous cells may be implanted between the two macrocapsules. In some embodiments, the components are implanted at sites distant from the primary tumor or metastasis in order to perform the vaccination in an immunologically un-disturbed location. However, in some embodiments, it is also possible to administer the vaccine composition in the vicinity of the tumor.

Five to seven days after implantation, the capsule is removed, for example using a hook, tether, or string attached to it. The antigenic component is not removed. Rather, it is progressively processed and removed by the patient's immune system via naturally occurring mechanisms.

The vaccination treatment with Onco-Maxi-Vax involves repeated immunizations. It is important to maintain a flexible vaccination schedule. For example, the vaccine composition may be administered subcutaneously for 4 weeks followed by two additional immunizations every two weeks. The repeated immunizations may be made at the same or similar locations on the patient's body. In one protocol, four different implantation sites are employed (e.g., both arms and both thighs), and vaccine implantation is rotated throughout each site during the course of treatment.

When used for cancer therapy, the dose of autologous tumor cells can be adjusted depending on the amount of cells harvested from the patients. It is recommended to have around $10^6$ to $10^7$ cells per immunization plus the cells required for testing (i.e., $28\times10^6$). Determination and/or adjustment of the dose of the autologous tumor cells is within the routine level of skill in the art.

In some embodiments, the tumor cells, which are the source of antigenic component, and the immuno-isolated allogeneic cells, which are the source of immunomodulatory component, are different, which is advantageous over prior vaccination strategies because the tumor cells do not need to be manipulated, other than being harvested and/or irradiated.

This anti-tumor immunization can be performed for a wide range of tumor types. As discussed above, the encapsulated immuno-isolated allogeneic cells are identical for every patient. However, the antigenic component is unique to the patient and may be obtained from tumor cells that can be harvested from a solid primary tumor, from a metastasis, and/or from fluid containing tumor cells (pleural, peritoneal, bone marrow or blood).

In clinical oncology, most patients present a primary tumor or metastatic lesion. However, not all tumors or metastases are equally easy to process. Therefore the type of tumor that will be tested needs to fulfil various criteria in terms of feasibility. Cancers that are likely to have a primary tumor that can be harvested include, but are not limited to: central nervous system tumor, such as glioblastoma; lung tumor (non-small cell lung cancer); prostate tumor; gastric carcinoma; breast carcinoma; lymphoma; pancreatic carcinoma; hepatocarcinoma (liver tumor); colon carcinoma; renal cell carcinoma; ovarian carcinoma; uterine carcinoma; sarcoma (soft tissue); leukemia (lymph node or blood); and/or multiple myeloma (blood, bone marrow, lymph-node, soft tissue).

Cancers that are likely to have metastases that can be harvested are dependent on the location of the metastasis. For technical reasons it is more difficult to harvest bone metastases than other localizations. These cancers may include, but are not limited to: head and neck carcinoma (lymph-node metastasis); lung cancer (lung, liver, soft tissue, brain, ; adrenal metastasis); prostate (non-bone metastasis); breast carcinoma (lung, liver, soft tissue, pleural fluid); gastric carcinoma (liver); pancreatic carcinoma (liver); colon carcinoma (liver); melanoma (lung, lymph-node, soft tissue, liver, brain); renal cell carcinoma (lung, liver); ovarian carcinoma (peritoneal or pleural fluid, liver); germinal tumors (lung); and/or bladder carcinoma (liver, lymph-node).

Any of the vaccine compositions, pharmaceutical compositions, and kits described herein can be used for therapeutic immunization against cancer or in a method of treating cancer. By way of non-limiting example, cancers that are treated may include, but are not limited to: lung cancer, melanoma, breast cancer, colon cancer, pancreatic cancer, kidney cancer, acute leukemia, chronic leukemia, glioblastoma, low grade lymphoma, high grade lymphoma, multiple myeloma, sarcoma, bone cancer, brain tumor, stomach cancer, esophageal cancer, head and neck cancer, thyroid cancer, bladder cancer, prostate cancer, ovarian cancer, uterine cancer, chordoma, and cervical cancer.

Following vaccination, tumor progression can be monitored used any method known in the art. For example, imaging such as CT scan can be used to record any change in tumor volume based on validated tools such as Response Evaluation Criteria In Solid Tumors (RECIST) criteria or immune related response criteria (irRC). Likewise, serological tumor markers including, but not limited to CA 153, CA19-9, CEA, AFP, NSE, CA 125 can be monitored.

Whenever possible, surgical resection of metastasis are attempted in order to document any changes in tumor structure. It is well described that classical tumor evaluation by bi-dimensional measurement may not be the best evaluation method to assess potential efficacy of immunization treatment. Destruction of the tumor cells can be very efficient and replaced with fibrous or inflammatory cells without detectable changes in size on radiological examination. Metabolic activity as assess by PET scan may be of relevance in this setting. The analysis of post immunization tumor lesion is of great interest for immunological analysis such as the characterization of the potential tumor antigen targeted by the treatment.

IA-Maxi-Vax

In another embodiment, any of the vaccine compositions described herein are used in the context of therapeutic or preventative immunization against various infectious diseases. This product is referred to as "IA-Maxi Vax" (infectious agent).

As with MVX-ONCO-1, "IA-Maxi-Vax" can be used as a therapeutic or preventative product (vaccine) made of two components that are physically in close proximity.

With IA-Maxi-Vax, the antigenic component contains one or more components from the infectious agents. Therefore all patients suffering from or at risk of developing a specific infection will be treated with the same product. Many known antigen components have been described in infectious diseases caused by viral, bacterial, parasitic, or fungal pathogens and are used currently for immunization strategies. Any of these antigens can be used as inactivated pathogens, infectious agent's lysates, protein extracts, recombinant proteins, peptides, DNA or other forms. In some conditions, depending on the infectious agent or the host medical condition, immunization is weak or non-protective leading to significant morbidity or mortality.

In the IA-Maxi-Vax vaccine composition, one component of the vaccine contains a combination of the antigen or a pool of antigens for a given infectious agent. As with MVX-ONCO-1, the other component of IA-Maxi-Vax is at least one biocompatible macrocapsule containing immuno-isolated allogeneic cells that secrete GM-CSF.

The vaccination treatment with "IA-Maxi-Vax" involves repeated immunizations at different subcutaneous sites. The total number of vaccination is dependent of the protocol and dosages and must be adjusted in each particular case. For example, the vaccination may require weekly injections for at least 2 weeks (e.g., 2, 3, 4, 5, 6, 7, or more weeks). Determination and/or adjustment of the dosages is within the routine level of skill in the art.

Examples of conditions that can be prevented or treated using "IA-Maxi-Vax" include, but are not limited to:

Viral Infections:

Target: HIV patients at various stage of their disease (early stage may be better candidates, with stronger immune system)

Target: CMV infection in specific condition (pre or post organ transplantation)

Target: recurrent herpes infection

Hepatitis B or Epstein Bar virus

Hepatitis C

Human papilloma virus (HPV)

Bacterial Infections:

Target: Mycobacterial infection is specific population such as HIV patients

Target *Helicobacter pylori*. *H. pylori* is the causative agent in the majority of the stomach ulcer or gastritis.

Parasitic Infections:

Malaria, Toxoplasma, Pneumocystis. Echinoccus

Fungal Infections:

*Candida, Aspergillus*

Delayed Type Hypersensitivity (DTH)

Delayed type hypersensitivity (DTH) reactions are inflammatory reactions initiated by mononuclear leukocytes. The term delayed is used to differentiate a secondary cellular response, which appears 48-72 hours after antigen exposure, from an immediate hypersensitivity response, which generally appears within 12 minutes of an antigen challenge. These reactions are mediated by T cells and monocytes/macrophages rather than by antibodies. They are also termed type IV hypersensitivity reactions.

In the context of tumor immunotherapy, DTH testing is performed with irradiated autologous tumor cells, injected intradermally in non-affected skin. At 24 and 48 hours, the presence and magnitude of the local inflammatory reaction is recorded by assessing the size of the thickened epidermis. DTH is performed before, during, and after the MVX-ONCO-1 therapy.

Usually, patients who convert a negative, pretreatment DTH into a positive DTH during and/or after treatment tend to exhibit a better outcome with the vaccine compositions described herein. As a result, it is useful to test patients for $DTH^+$ response prior to vaccination. $DTH^+$ response testing requires at least $3 \times 10^6$ cells: $1 \times 10^6$ cells before vaccination; $1 \times 10^6$ cells at weeks 5-6; and $1 \times 10^6$ cells after vaccination at week 12.

Preferably, DTH response is tested on an opposite part of the body from the capsule implantation site.

The determination of the appropriate dosing schedule and/or implantation site is within the routine level of skill in the art. One non-limiting example of a dosing schedule is shown in the following table:

| Day (D) −3 | D 0 (Week 1) | W 2 | W 3 | W 4 | W 5 | W 6 | W 7 | W 8 | W 9 | W 10 | W 14 |
|---|---|---|---|---|---|---|---|---|---|---|---|
| DTH | Vaccine (V) 1 | V2 | V3 | V4 | Off (remove V4) | V5 DTH2 | Off (remove V5) | V6 | Off | Off | DTH3 |

At least $28 \times 10^6$ cells or more are needed for the complete vaccination and testing protocol:

$6 \times 4 \times 10^6$ cells for vaccination;

$3 \times 1 \times 10^6$ cells for DTH testing; and $0.5 \times 10^6$ irradiated cells and $0.5 \times 10^6$ non-irradiated cells, which are cultured for 10 days and counted. There must be $<0.5 \times 10^6$ cells in the irradiated aliquot. This test is performed in order to ensure that the cells have been properly irradiated.

Pharmaceutical Compositions and Kits

Also provided herein are pharmaceutical compositions and kits containing the vaccine compositions described herein. All these products are particularly well suited for industrial production because they are easy to produce in large amount thanks to the "universal" characteristic of the device. As the allogeneic cells are immuno-isolated, the same encapsulated cells are suitable for all the patients. This "universal" characteristic is particularly interesting for cancer therapy, where multiple injections of the vaccine or the pharmaceutical composition are required.

A pharmaceutical composition according to the present invention contains the pharmaceutical compositions combined with a physiologically and/or pharmaceutically acceptable carrier. Any suitable physiologically or pharmaceutically acceptable carrier known in the art can be used. Such compositions may also contain any pharmaceutical additive necessary for the survival of the cells and for the success of the administration or implantation.

Provided herein are kits including the vaccine compositions described herein along with instructions for use.

Also provided are uses of any of vaccine compositions, pharmaceutical compositions, and kits for use in therapeutic and/or preventative vaccination as well as methods of therapeutic and/or preventative vaccination using any of the vaccine compositions, pharmaceutical compositions, and/or kits described herein. For example, the vaccination may be cancer therapeutic vaccination or therapeutic or preventative vaccination against infectious agents. For cancer immunization, the patient is typically suffering from the disease prior to treatment. For infectious agent immunization, the patient is suffering from or is a risk of developing the disease or disorder.

The subject is preferably a human patient, but animals are also contemplated. A subject can be in need of vaccination for different reasons, because a preventive immunization is preferable, like for benign disease, or is necessary for example in the case of severe epidemics.

Infectious agent immunization can be preventative because the patient will be in contact with the antigenic component sooner or later. Likewise, infectious agent immunization can also be therapeutic because the patient has already been in contact with the antigenic component but is not able to generate an adequate immune response by himself Different vaccination protocols can be used depending on the nature of the vaccination desired. Administration of both components can be made simultaneously, separately, or sequentially. It can be advantageous to temporally dissociate the administrations. In fact, because the allogeneic cells are immunoisolated in biocompatible macrocapsules, they typically have a long-lasting effect. In contrast, the antigenic component is likely to be processed and eliminated very rapidly by the host's immune system. In such a case, when the administration of the components is dissociated, the administration of antigenic component can be repeated, with a single administration of the immuno-isolated allogeneic cells.

The antigenic and the immunomodulatory agents should be co-localized in order to produce an optimized effect.

For an optimized immunization process, the administration is repeated several times at regular intervals. For example, when the preventative or therapeutic vaccination is cancer therapy or vaccination, the regular intervals are weekly injections for four weeks followed by two additional immunizations every two weeks. Likewise, when the preventative or therapeutic vaccination is infectious agent therapy or vaccination, the regular intervals is weekly injections for two weeks.

In some embodiments, the vaccine composition is administered to a subcutaneous location because this region is rich in dendritic cells. However, those skilled in the art will recognize that the administration can be made intradermally or at any other location likely to favor the expected immune response. For example, the administered composition may be injected, ingested, implanted, applied, or any other administration means.

The invention having been described, the following examples are offered by way of illustration and not limitation.

EXAMPLES

Example 1

An Open Phase I Clinical Study Assessing the Safety and Tolerability of MVX-ONCO-1 in Patients with Solid Tumor Who are not or not any Longer Amenable to any Standard Therapy (Clinical Trial NCT02193503)
Objectives:

The objective of the study was to assess the safety and tolerability of 6 vaccine doses of MVX-ONCO-1, a clinical grade encapsulated cell therapy (ECT) product, administered subcutaneously (injections and capsule implantations), in patients with advanced metastatic solid tumor in progression who are not or not any longer amenable to any standard therapy of their tumor disease.
Endpoints:

The primary endpoint of the study was to assess safety and feasibility parameters including adverse and serious adverse events (incidence, causality, severity), local and systemic tolerance to the administered study treatment, changes in laboratory values and vital signs in patients with solid tumor. The secondary endpoint of the study was to assess clinical activity and immunomonitoring (e.g., measure some tumor responses in using imaging technique, serological tumor markers, and metabolic monitoring).
Study Design:

This was an open label, phase I study that included 15 patients with progressing, solid tumors refractory or not amenable to standard chemotherapy.

For ethical reasons, performing surgical procedure in the sole goal to obtain tumor material for this study is not acceptable. Therefore, tumor material was only be available from patients undergoing pleural or ascite tap for removing fluid containing malignant cells or patient undergoing surgery that was required for medical reason not related to the clinical protocol.
Tumor Tissue Procurement: Pre-Surgical and Surgery Patients signed pre-surgical and clinical informed consent forms, which granted permission to use and manipulate extra tumor tissue for the production of autologous tumor cell vaccines.
Surgical and Histopathological Documentation The patient's autologous cells were harvested in the operating room or through sterile procedures to access tumor cells (ascite tap, pleural fluid, bone marrow, CT-guided biopsy). The operative report for the cell harvest included a description of the operative findings, with specific reference to extent of disease and whether or not any adjacent organs were removed with the specimen.
Dissociation and Autologous Tumor Cell Vaccine Manufacturing Processing of tumor cells for vaccine preparation was done on tissue obtained from each individual patient. The dissociation and the vaccine doses manufacturing was conducted under current Good Manufacturing Practices (cGMP) conditions under strict adherence to aseptic techniques in accordance with LTC standard operating procedures (SOPs). Once the process was completed, the cells were frozen and stored in the vapor phase of liquid nitrogen of a dedicated tank.

Treatment and Short Term Follow-Up

Immunizations were performed in healthy skin, distant from the tumor deposits. Patients were treated with 6 subcutaneous sc immunizations (week 1-2-3-4-6-8) combining $4 \times 10^6$ irradiated autologous tumor cells and 2 macrocapsules containing each $8 \times 10^5$ MVX-1 cells genetically engineered to produce>20 ng/24 h of huGM-CSF over 7 days.

Eligible patients received the vaccine treatment every week starting at Study Day 1 (SD1), for 4 weeks followed by two additional injections, 2 weeks apart. The safety and efficacy analysis was performed at the end of the study W18 (9 weeks for a complete vaccination cycle+9 weeks of follow-up). The tumor size was assessed at baseline and at W6, W12 & W18.

Macrocapsules were removed after 7 days and analyzed for huGM-CSF production.

Long Term Follow-Up

Patients will be followed-up for safety until death or Year 5 after SD1 whichever comes first. Moreover, patients were withdrawn from the study for major protocol violations, uncontrolled serious intercurrent illness or serious adverse events, non-compliance to protocol or administrative reasons.

Study Population:

The study population included patients with advanced metastatic solid tumor in progression, who are not or not any longer amenable to any standard therapy of their tumor type.

Inclusion Criteria:
- Male or female patients aged 18 years and older with advanced metastatic cancer in progression of various sites [carcinoma of lung (either small cell or non-small cell), colon, breast, pancreas (exocrine or endocrine), stomach, esophagus, head&neck, thyroid, kidney, bladder, prostate, ovary, uterus (cervix or corpus); sarcoma of soft tissue, bone, uterus, melanoma; primary brain tumor] where all recognized treatments exhausted or not feasible
- Life expectancy: estimate of at least 4 months
- Performance status grade 0-2 (WHO grading)
- No major impairment of liver function (ALT <2.5 times the upper limit of normal range, Bilirubin within the normal range (exception: liver metastases: ALT <5 times ULN; Bilirubin <3 times ULN)
- No major impairment of renal function (creatinine ≤1.5 times the upper limit of normal range)
- No major impairment of bone marrow function (hemoglobin >9.0 g/dl WBC >2.5×$10^9$/L, neutrophils ≥1.5× $10^9$/l, Thrombocytes ≥50×$10^9$/l)
- Primary tumor and or metastasis amenable for partial/total surgery or tap and subsequent cell harvesting estimate >27×$10^6$ cells
- Ability to understand the concept of a clinical trial
- Able to understand patient information form and inform consent form
- Has given written informed consent Exclusion Criteria:
- Have participated in any other investigational study or received an experimental therapeutic procedure considered to interfere with the study in the 4 preceding weeks
- Have received any chemotherapy treatment in the 4 preceding weeks
- Serious concomitant disease
- History of second cancer that was treated with curative intent and in complete remission for <5 years
- Patient with a systemic disease other than cancer, that is not controlled by usual medication
- Untreated brain metastasis (screening CT or MM mandatory even for asymptomatic patients). Patient with history of brain metastasis with no evidence of brain relapse after surgery/radiotherapy at screening can be enrolled
- Chronic immunosuppressive treatment including steroids >30 mg cortisone or equivalent/day
- Therapeutic anticoagulation with coumarine or continuous iv heparin. Low-molecular weight heparin (LMWH) is permitted as long as treatment can be withheld several hours prior to subcutaneous implantation
- Positive HIV-1, HIV-2, HTLV-1, hepatitis B surface antigen, or hepatitis C antibody
- Females of child-bearing potential who are pregnant or lactating or who are not using adequate contraception (surgical, hormonal or double barrier, i.e. condom and diaphragm).
- Known allergy to reagents in the study product (MVX-ONCO-1) like, penicillin, streptomycin.

Investigational Medicinal Product (IMP):

For manufacturing reasons, non-adherent cells (excluding fibroblasts or epithelial cells), which can easily be stored frozen can be used. For safety reasons, only biosafety level 1 cells were tested. Five different cell lines were tested for their ability to undergo encapsulation: CCL243, CCL246, CCL246.1, TIB202, and CRL1582. CCL243 (a cell of hematopoietic origin) was finally selected and subsequently genetically modified to express huGM-CSF. MVX-1 is the cell line obtained from single cell cloning of the genetically modified CCL243 cell line.

MVX-ONCO-1 is a form of active specific immunotherapy (ASI), a process by which the patient's immune response to tumor cells is stimulated and/or augmented.

MVX-ONCO-1 is a patient specific, cell-based, immunotherapy composed of:
a. an immunomodulator (GM-CSF: granulocyte-macrophage colony stimulating factor) released from an immuno-protected, macroencapsulated, allogeneic, genetically modified cell line (MVX-1), and
b. irradiated, autologous tumor cells as source of antigen.

Capsules loaded with MVX-1 cells were selected for their ability to efficiently be frozen for long term storage up to 18 months (i.e., up to 1, 2, 3, 4, 5, 6, 7, 8, 9, 10, 11, 12, 13, 14, 15, 16, 17, or 18 months). Macrocapsules loaded with MVX-1 cells are processed and stored frozen.

Vaccine Dose:

One implantation consisted of two macrocapsules containing the MVX-1 cell line genetically engineered to release stable quantity of GM-CSF over 7 days (>20 ng/24 hours) and a minimum of $4 \times 10^6$ lethally irradiated autologous tumor cells.

All therapeutic products were processed in good manufacturing (GMP) conditions.

Administration:

Under local anesthesia, the two macro capsules were implanted subcutaneously 1 cm apart, in a parallel manner. The irradiated autologous cells were injected subcutaneously between the two capsules. Patients were treated only if a minimum of $27 \times 10^6$ irradiated, autologous tumor cells were available (6 vaccines with $4 \times 10^6$ cells+3 delayed type cutaneous hypersensibility testing with $1 \times 10^6$ cells).

Dosage and Schedule:

No data existed in the literature regarding the optimal quantity of antigenic load. Therefore in this first clinical trial, the tumor cell numbers were not escalated. For patients on trial showing either a stable disease or partial/complete response, prolonged immunization was offered once a month if autologous cells were still available after the first 6 injections.

Two biocompatible macrocapsules each loaded with $8 \times 10^5$ MVX-1 cells producing humanGM-CSF and a subcutaneous injection of $4 \times 10^6$ irradiated autologous tumor cells were administered weekly for four weeks. Two additional administrations were given every two weeks. Seven days after implantation (i.e., on day 8 following an implantation), the macrocapsules were explanted.

Data Analysis and Statistics:

Data management and statistical analysis was conducted once the last enrolled patient has completed the W18 assessment. All efficacy parameters were analyzed descriptively. Supplementary analysis was conducted at regular intervals depending of the patient survival curve.

Patient characteristics assessed during the screening phase were tabulated for visual comparison. For quantitative variables, the following descriptive statistics were given: N, Mean, Standard Deviation, Minimum, Median and Maximum values; for qualitative variables, the Frequency and Percentage of patients were provided.

The following parameters were described at baseline:
Patient demographics
Baseline disease characteristics, including diagnosis, status of disease activity, previous treatments.
Secondary condition, including therapies.
Medical history.
Prior and concomitant medication Estimated Accrual:

For safety reasons, the second patient received vaccination only after the first patient had undergone the first 4 vaccines. The same waiting/observational period was observed for the third patient who received vaccination only after the second patient had undergone his/her first 4 vaccines. Subsequently, accrual averaged one participant every 2 weeks (24 additional weeks for 12 patients).

Study Duration by Patient:

Screening+ cell harvest+ vaccine doses manufacturing (2 weeks)+1 complete vaccination treatment (9 weeks)+ follow-up (9 weeks): about 6 months.

A summary of the Study Flow Chart is provided in the following table:

| Visit | Summary of Visit |
|---|---|
| Baseline | Screening |
| Week −2 | Cell Harvesting (from surgery, biopsy, or tap). A minimum of $27 \times 10^6$ cells must be harvested for study inclusion. |
| Day −5 | Delayed-type hypersensitivity performed. |
| Day 1 | Subcutaneous implantation of the two macrocapsules plus subcutaneous autologous irradiated cell injection at first site. |
| Day 8 | Removal of the previously implanted capsules and implantation of new capsules. |
| Day 15 | Removal of the previously implanted capsules and implantation of new capsules. |
| Day 22 | Removal of the previously implanted capsules and implantation of new capsules. |
| Week 5 | Removal of the previously implanted capsules. |
| Week 6 | Implantation of new capsules. |
| Week 7 | Removal of the previously implanted capsules. |
| Week 8 | Implantation of new capsules. |
| Week 9 | End of treatment period. Removal of the previously implanted capsules. |
| Week 10 | Follow-up (serological tumor markers, tumor pain, hematology and serum chemistry, electrophoresis and immunoglobulins, safety urine sample) |
| Week 12 | Follow-up (assessment of tumor size, imaging, tumor pain, hematology and serum chemistry, electrophoresis and immunoglobulins, safety urine sample) |
| Week 14 | Follow-up (serological tumor markers, immune monitoring, tumor pain, hematology and serum chemistry, electrophoresis and immunoglobulins, safety urine sample) |
| Week 18 | Follow-up (assessment of tumor size, imaging, serological tumor markers, tumor pain, hematology and serum chemistry, electrophoresis and immunoglobulins, safety urine sample) |
| Post treatment follow up | After Week 19, patients are followed-up for safety every three months until death of Year 5, whichever comes first. |

Results:

All 15 patients included in the therapeutic trials have been treated. MVX-ONCO-1 for each patient was manufactured successfully, according to GMP and SOP of the clinical trial, and all bacterial testing for endotoxins and/or mycoplasma on MVX-ONCO-1 was negative.

None of the prepared therapeutic vaccine composition had to be discarded due to quality concerns.

Cancer types treated with MVX-ONCO-1 include ovarian, head and neck, pancreatic, prostatic, and colorectal. To date, 77 vaccine have been administered.

The level of GM-CSF secretion from loaded capsule before subcutaneous implantation was within specified limits in all of the cases. Additionally, all subcutaneously implanted macrocapsules were successfully removed 7 days after implantation. Once removed, all of the macrocapsules were tested for subsequent GM-CSF release and all demonstrated stable, high levels of secretion. One capsule broke following removal.

No suspected unexpected serious adverse reaction (SUSAR) was observed in conjunction with this trial. Moreover, no serious adverse events (SAE) or systemic adverse events (AE) were reported related to the MVX-ONCO-1 product. Rather, all SAEs were related to disease progression. Twenty-two related AE were reported, but none were serious. Six were due to minor defects in the macrocapsules, which lead to one grade 2 and five grade 1 implant site traumas. Of the 16 reported non-serious drug-related adverse drug reactions, 12 were grade 1 implant site hematomas, 3 were grade 1 mild fever, and 1 was a grade 3 vaso-vagal reaction. Grade 1-2 local AE at the site(s) of vaccination included pain during implantation, local discomfort, and/or limited inflammation.

A summary of the feasibility results is provided below:

| Feasibility | N (%) |
|---|---|
| Screened/Enrolled | 24/15 patients |
| Enrolled/Treated | 15/15 patients |
| Tumor processed successfully | 15 (100) |
| Successful capsules manufacturing and implantation | 144 (100) |
| GMP quality IMP (capsules and irradiated tumor cells) | 220/221 (99.5) |
| GM-CSF secretion >20 ng/24 hrs. before implantation/after implantation | 144(100)/143(99.3) |

Accordingly, the results of this study indicate that the MVX-ONCO-1 product is safe and very well tolerated, and these results indicate that manufacturing clinical grade IMP and treating patients with this innovative strategy is feasible. Additionally, the MVX-ONCO-1 product is also robust, as 99.5% GMP grade IMP.

At the end of the short term follow-up (week 18) 6, patients (40%) were alive and 9 have died (60%). In the long term follow-up, 4 patients died, and two patients were alive.

The overall survival (OS) ranged from 46 days to 441 days (mean: 199 days (SD: 121 days), median 134 days). Following the RECIST 1.1. criteria, 2 out of 15 patients (13.33%) showed a partial response and 6 (40.00%) showed a stable disease as the best overall response at any time point.

Figure 5:
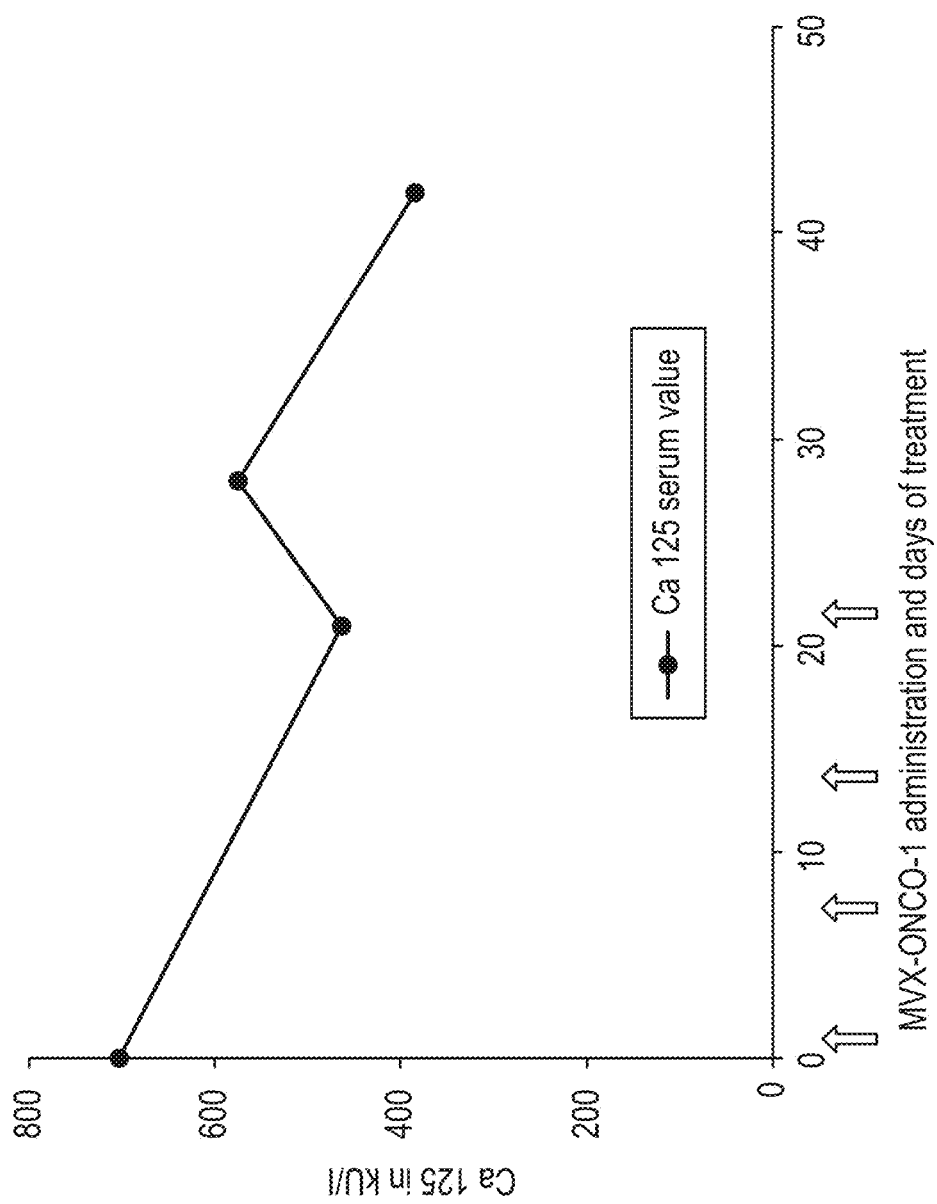
FIG. 5 is a graph showing Ca 125 serum marker reduction in advanced refractory ovarian cancer following MVX-ONCO-1 treatment.
Figure 6:
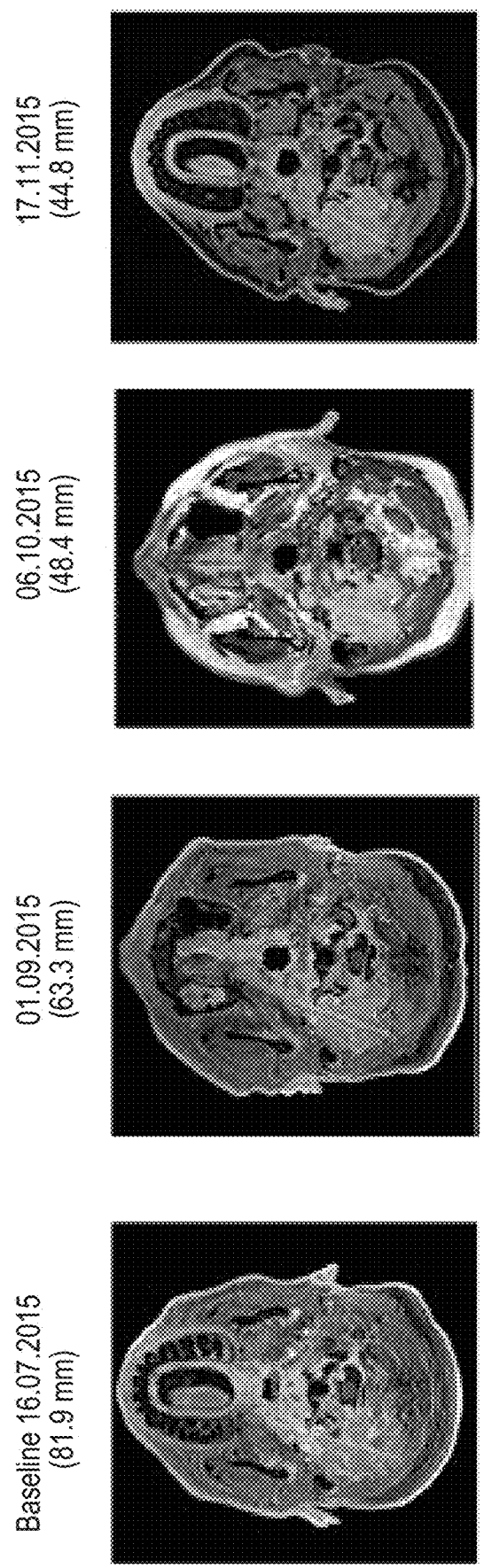
FIG. 6 shows the MM results before, during, and after treatment in a patient with refractory, relapsing chordoma. Partial response is documented and ongoing for more than 12 months.
Figure 7C:
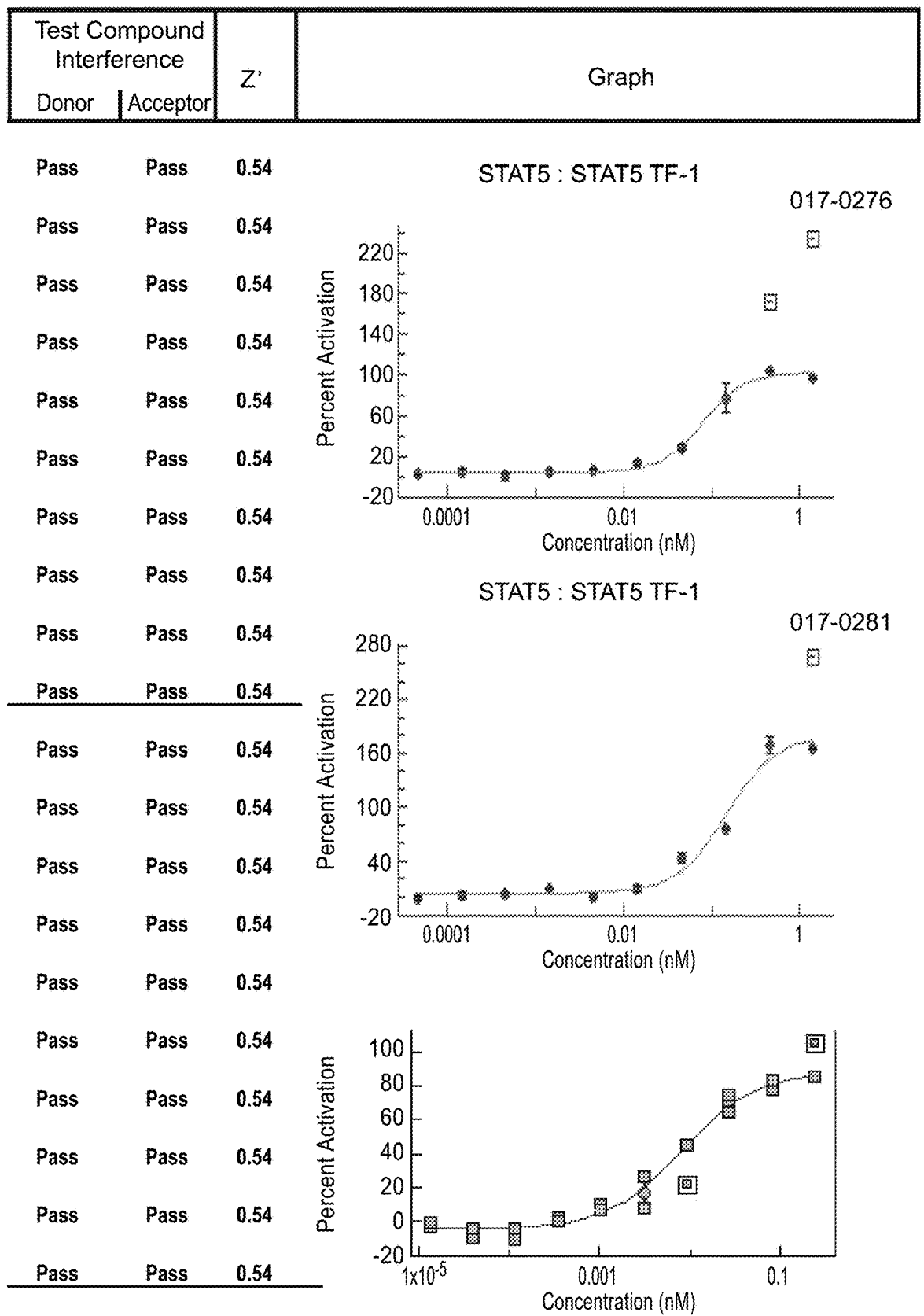

A summary of the efficacy results is provided below:

| Cancer | Number of Patients | Clinical Outcome |
| --- | --- | --- |
| Head&Neck | 3 | Prolonged survival, response on lung mets (i.e., decrease in pulmonary metastases of a squamous cell carcinoma (see FIG. 4). Decrease in chordoma size (see FIG. 6). |
| Ovarian | 6 | 1 decrease in tumor markers (i.e., close to 50% decrease in serum level of Ca125 (see FIG. 5)), 1 prolonged survival, 3 progressive disease (PD), 1 stable disease (SD) at W6 |
| Pancreas | 3 | 1 SD at 6 weeks, 1 SD at week 12, 1 PD |
| Prostate | 1 | PD |
| Colon | 2 | 1 SD and 1 PD |

Conclusion:

This first in man trial demonstrated the very good safety profile as well as the feasibility of this novel patient specific cell-based immunotherapy. Moreover, secondary endpoints showed clinical benefit for a significant portion of patients with advanced, progressing, refractory solid malignancies. The early analysis of immunomonitoring parameters shows that patients able to induce a Delayed type hypersensitivity reaction to their own tumor cells upon immunization with MVX-ONCO-1 tend to have a better survival. In addition, preliminary analysis of lymphocytes subsets, before, during and after immunization with MVX-ONCO-1 in one patient with prolonged partial response showed an antigen specific immune response.

Phase 2 trials with MVX-ONCO-1 are planned in several tumor types (e.g., advanced pancreatic carcinoma, ovarian carcinoma, and/or Head&Neck squamous cell carcinoma) as well as combination therapies with immune check-point modulators. For example, the following Phase IIa clinical trials (with no control arm) are contemplated:

MVX-ONCO-1 in Head&Neck cancers

MVX-ONCO-1 as a single agent in lung cancer

MVX-ONCO-1 in combination with chemotherapy, as an adjuvant to improve efficacy in ovarian cancer after recurrence following standard first-line therapy of Taxol and Carboplatin MVX-ONCO-1 as a single agent in pancreatic cancer Clinical trials involving Head & Neck cancers are contemplated because:

cells can be harvested from these tumors easily, the cancers typically have a poor prognosis (<6 months), they are frequently occurring cancers, these tumors are PD1/PDL-1 responsive, and as such, they are immunogenic tumors The endpoint of these studies will be overall survival rate at 6 months.

Example 2

Harvest of Autologous Tumor Cells (Antigenic Load)

A tumor mass (primary lesion or metastasis) from the patient to be treated was surgically harvested. A standard pathological examination was performed on a portion of the mass in order to confirm the malignant nature of the harvested material. It was then processed in order to obtain a single cell suspension. This was performed by both mechanical and enzymatic methods.

The tumor mass was first cut in smaller pieces using dissecting microscope, then the tumor was put into a sterile bag with a sterile solution containing various enzymes (collagenase). The bag was inserted into a cell blender (Stomacher Lab System) that processed the product into a cell suspension. The combination of enzymatic and mechanical activities at 37° C. for few hours allowed the efficient dissociation of the extra-cellular matrix of the tumor and turned it into single cell suspension. This was performed in serum free solution.

The cells were then washed three times with HBSS using a refrigerated centrifuge (Sorvall) 4° C., 5 minutes, 700 rpm, and resuspended in HBSS. Cells were then counted using Trypan blue (Fluka) solution and a Neubauer chamber.

The cells were resuspended at a chosen concentration, irradiated at 10000 rads in an irradiator devoted for clinical use, aliquoted and frozen in freezing media containing 10% DMSO.

Example 3

Immuno-Isolated Cytokine Provider a) Generation of GM-CSF Producing Cells.

The cells to be introduced into the capsules were allogeneic (obtained from a human cell line). In order to prevent un-predicted toxicity, cell lines that have already been approved in clinical protocols such as immortalized fibroblasts or myoblasts were used. These cells were first stably transfected with human GM-CSF cDNA.

Two methods of transfection were used: retroviral and electroporation. For retroviral transfection, hGM-CSF cDNA was inserted in-frame into the MFG retroviral vector and transcription was driven by the LTR of the virus. The plasmid did not contain any selection marker or antibiotic resistance gene.

For the transfection by electroporation, hGM-CSF cDNA as under the CMV promoter and the plasmid contains a selective marker (such as an antibiotic resistance gene).

Different types of cells for transfection and different GM-CSF plasmids can also be sued, which leaves more flexibility with respects to local health department regulations.

The cytokine producing cells was cultured in serum free media at 37° C. with 5% CO2 using standard techniques. Harvesting was performed as follow: The supernatant of confluent, adherent cells in a 10 cm culture plate was removed and the cells were washed once with 5 ml of autoclaved Phosphate buffered Saline (PBS) for 5 minutes at 37° C. PBS was then removed and 2 ml of Trypsin-EDTA 0.5% (Life Technologies N°25300054) was added and the cells were incubated for four minutes at 37° C. The trypsin/EDTA allowed the detachment of the adherent tumor cells. The cells were then harvested with a 2 ml pipet and diluted into 5 ml of Hank's balanced salt solution (HBSS Life Technologies N°24020091). The cells were washed three time with HBSS using a refrigerated centrifuge (Sorvall) 4° C., 5 minutes, 700 rpm) and resuspended in HBSS. Cells were then counted using Trypan blue (Fluka) solution and a Neubauer chamber.

The quantity of hGM-CSF produced and secreted by the cells was evaluated Elisa (R&D system and Pharmingen kits) on filtered cell's supernatant. This analysis allowed the selection of the best cytokine producing cell-line.

b) Immuno-Isolation of Cytokine Producing Cells

In order to ensure sustained release of cytokine by allogeneic cells and allow repeated immunization it was necessary to immuno-isolate the cytokine producing cells from the recipient's immune system. This was performed by either macroencapsulation.

The cytokine producing cells were loaded into macrocapsules. Any of the macrocapsules described herein can be utilized. The capsule was loaded with the cell suspension at a rate of 10.5 ul/min. Sealing of the capsule was obtained by polymer glue, but could also be done by heating or surgical clips. Analysis from supernatant of encapsulated cells containing GM-CSF secreting cells showed that a stable, continuous release of GM-CSF was achieved for at least fifteen days after loading, with cytokine levels that are around 70 ng/$10^5$cells/24 hrs.

Example 4

Immunization

Immunization with Onco-Maxi-Vax required the subcutaneous injection in close contact of the two components of the vaccine composition.

The capsule containing the cytokine producing cells was placed in the subcutaneous tissue using a small skin incision under local anesthesia. The skin was closed with surgical tape.

The irradiated tumor cells from the patient (=antigenic load) were thawed, washed two time with 0.9% NaCl, sterile solution and then injected, subcutaneously, in very close vicinity to the capsule, using a 24 gauge needle.

Vaccination was repeated at regular intervals. The site of vaccination was different at each immunization (abdominal wall, upper arms, thighs, thorax, etc.).

Example 5

Comparative Data

Efforts were made to optimize the "universal" component of the vaccine compositions described herein by making various improvement and/or changes to the capsules described in the prior art (e.g., WO 2003/105895).

For example, the vaccine compositions described herein preferably utilize non-adherent cell types within the macrocapsules. Moreover, the MVX-1 cell line is hematopoietic in origin, as opposed to previous devices, which contemplated the use of cells of fibroblast or epithelial origin.

In addition, the vaccine compositions, uses, and methods described herein utilize novel freezing methods and a distinct GMP conditioning regimen that were not used in the compositions described in WO2003/105895.

Example 6

GM-CSF Biological Activity Assay

A functional cell-based assay was performed in order to determine the biological activity of the GM-CSF produced by the MVX-1 cell line. Two samples of the cell supernatant containing the produced GM-CSF were tested in duplicate using the LanthaScreen™ Cellular Assay (ThermoFisher Scientific), which uses time-resolved resonance energy transfer (TR-FRET) between a terbium-labeled phosphorylation-site specific antibody (PSSA) and a green fluorescent protein (GFP fusion of a particular kinase substrate to provide an assay readout that is ratiometric, robust, and amenable to high-throughput screening (HTS) applications. The use of a GFP fusion of the target along with a single detection antibody simplifies the assay protocol, eliminates the need for beads or additional reagents, and simplifies the assay relative to other two-antibody "sandwich" approaches.

Assay Conditions

Test Compounds

All Test Compounds are initially prepared at a 1000× concentration in 100% DMSO. Serial dilutions (½ log) of the Test Compounds are prepared in DMSO. The Known Inhibitor is prepared in this same manner.

Assay Plate

Corning 384-well white, flat bottom, polystyrene, tissue-culture treated assay plate (Corning #3570).

Assay Media

LanthaScreen Cellular Assays are typically run in low-serum (or serum-free media) in order to lower pathway activation and provide a baseline for subsequent analyses.

Lysis Buffer

The complete LanthaScreen Cellular Assay Lysis Buffer consists of 20 mM Tris-HCl, pH 7.4, 5 mM EDTA, 5 mM NaF, 150 mM NaCl, 1% NP-40 (or equivalent), protease inhibitor cocktail (Sigma #P8340), phosphatase inhibitor cocktail (Sigma #P2850), and 2 to 5 nM of the appropriate Tb-PSSA.

Agonist Assay Protocol (General)

1. 32 μL of cells diluted in Assay Media to appropriate cell density are added to the assay plate. If needed, cells are incubated at 37° C./5% CO2 for 0 to 24 hours (depending upon cell line specifics) before compound is added.

2. 40 nL of 1000× compound or known activator titration is added to the cells in the assay plate. 8 μL of Assay Medium is added to these wells.

3. 8 μL of Assay Medium is added to remaining control wells to bring the volume up to 40 μL.

4. The assay plate is incubated at 37° C./5% CO2 in a humidified incubator for a pre-determined length of time (cell line/assay specific).

5. Cells are lysed by the addition of lysis buffer with a pre-determined concentration of Tb-labeled Ab (assay specific).

6. The assay plates are incubated in the dark at room temperature for a pre-determined length of time (assay specific).

7. Read plate on a fluorescence plate reader.

Antagonist Assay Protocol (General)

1. 32 μL of cells diluted in Assay Media to appropriate cell density are added to the assay plate. If needed, cells are incubated at 37° C./5% CO2 for 0 to 24 hours (depending upon cell line specifics) before compound is added.

2. 40 nL of 1000× compound or known inhibitor titration plus 4 μL of assay media is added to the cells in the assay plate and incubated for 30 minutes at 37° C./5% CO2 in a humidified incubator.

3. 4 μL of the EC80 concentration of activator, as determined in an Activator assay, is added to all wells containing test compound and known inhibitor to bring the final assay volume to 40 μlL.

4. 4 μL of Assay Medium is added to remaining control wells to bring the volume up to 40 μL.

5. The assay plate is incubated at 37° C./5% CO2 in a humidified incubator for a pre-determined length of time (cell line/assay specific).

6. Cells are lysed by the addition of lysis buffer with a pre-determined concentration of Tb-labeled Ab (assay specific).
7. The assay plates are incubated in the dark at room temperature for a pre-determined length of time (assay specific).
8. Read plate on a fluorescence plate reader.

Assay Controls

The following controls are made for each individual assay, on every assay plate: MAX STIM Control (If Applicable)

The maximum TR-FRET signal (Emission Ratio; 520 nm/490 nm) is established by the MAX STIM Control (or the 0% Inhibition Control). These control wells contain GFP+ cells stimulated with an EC100 concentration of agonist in the presence of 0.1% DMSO.

UNSTIM Control

The minimum TR-FRET signal is established by the UNSTIM Control. These control wells contain unstimulated cells in the presence of 0.1% DMSO.

EC80 Control (Inhibitor Mode Only)

The EC80 control is a concentration of the known activator in assay media that has been determined through an activator experiment. In inhibitor mode, the EC80 control is used to determine the actual baseline of activation or 0% inhibition.

0% Inhibition

The TR-FRET signal obtained from wells containing cells stimulated with an EC80 concentration of agonist in the presence of 0.1% DMSO (no compound present).

Known Inhibitor Titration (If Applicable)

A Known Inhibitor control standard curve (10-point titration) is run on each assay plate to ensure that the assay is inhibited within an expected $IC_{50}$ range.

The relevant LanthaScreen Cell Lines Available for Screening are provided below:

| Assay | Cell Line | Technology | Activator | EC50 (nM) | Inhibitor | IC50 (nM) | Act. Mode | Inh. Mode |
|---|---|---|---|---|---|---|---|---|
| STAT5 | STAT5 TF-1 | LS | GM-CSF | 0.003 | JAK Inhibitor I | 37.3 | Yes | Yes |

*EC50 and IC50 values are representative

STAT5 A/B [pTyr694/699]—LanthaScreen STAT5 TF-1—Activator Screen, GM-CSF Stimulation Cells are thawed and resuspended in Assay Media (OPTI-MEM, 0.5% csFBS, 0.1 mM NEAA, 1 mM Sodium Pyruvate, 100 U/mL/100 μg/mL Pen/Strep) to a concentration of 3,125,000 cells/mL. 32 μL of the cell suspension is added to each well of a white TC-Treated assay plate (100,000 cells/well) and incubated for 16-24 hours at 37° C./5% CO2 in a humidified incubator. 40 nL of the control activator GM-CSF or test compound is added to the appropriate assay wells followed by an addition of 8 μL of Assay Media. The assay plate is incubated for 30 minutes at 37° C./5% CO2 in a humidified incubator. 30 μL of LanthaScreen Cellular Assay Lysis Buffer containing 5 nM of LanthaScreen anti-STAT5 A/B [pTyr694/699] antibody and 10 nM of Tb-anti-Mouse antibody is added to the wells. The assay plate is incubated for 120 minutes at room temperature. The assay plate is read with a fluorescent plate reader.

STAT5 A/B [pTyr694/6991]—LanthaScreen STAT5 TF-1—Inhibitor Screen, GM-CSF Stimulation Cells are thawed and resuspended in Assay Media (OPTI-MEM, 0.5% csFBS, 0.1 mM NEAA, 1 mM Sodium Pyruvate, 100 U/mL/100 μg/mL Pen/Strep) to a concentration of 3,125,000 cells/mL. 32 μL of the cell suspension is added to each well of a white TC-Treated assay plate (100,000 cells/well) and incubated for 16-24 hours at 37° C./5% CO2 in a humidified incubator. 40 nL of the control inhibitor JAK Inhibitor I or test compound is added to the appropriate assay wells followed by an addition of 4 μL of Assay Media. The assay plate is incubated for 30-60 minutes at 37° C./5% CO2 in a humidified incubator. 4 μL of 10× control activator GM-CSF at the pre-determined EC80 concentration is added to wells containing the control inhibitor or compounds. The assay plate is incubated for 30 minutes at 37° C./5% CO2 in a humidified incubator. 30 μL of LanthaScreen Cellular Assay Lysis Buffer containing 5 nM of LanthaScreen anti-STAT5 AB [pTyr694/699] antibody and 10 nM of Tb-anti-Mouse antibody is added to the wells. The assay plate is incubated for 120 minutes at room temperature. The assay plate is read with a fluorescent plate reader.

The results of this assay were all positive (see FIGS. 7A-D). The GM-CSF produced by the MVX-1 cell line was deemed equivalent to commercially available GM-CSF, within the limitations of the assay.

EQUIVALENTS

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

The foregoing description has been presented only for the purposes of illustration and is not intended to limit the invention to the precise form disclosed, but by the claims appended hereto.

The invention claimed is:

1. A method of treating cancer in a patient comprising administering an effective amount of:
   a) an autologous source of tumor antigens prepared according to a method comprising
      i) obtaining a solid tissue sample comprising autologous tumor cells;
      ii) digesting the solid tissue sample using an enzyme;
      iii) further mechanically digesting the solid tissue sample;
      iv) inactivating the enzyme; and
      v) isolating single tumor cells from the solid tissue sample to obtain a cell-suspension comprising an autologous source of tumor antigens; and b) at least one retrievable biocompatible macrocapsule comprising between about $5\times10^5$ and about $1\times10^6$ immuno-isolated allogeneic cells that secrete at least 20 ng/24 hour of GM-CSF, wherein the at least one biocompatible macrocapsule comprises:
  i) a core comprising allogeneic cells and an internal coil wherein the distance between spires on the internal coil is about 1 mm±0.1 mm, wherein the allogeneic cells are distributed on the internal coil; and
  ii) a semipermeable membrane surrounding the core that permits diffusion of GM-CSF there through.

2. The method according to claim 1, wherein the at least one biocompatible macrocapsule and the autologous source of tumor antigens are implanted and the at least one biocompatible macrocapsule is subsequently removed.

3. The method according to claim 2, wherein the at least one biocompatible macrocapsule and the autologous source of tumor antigens are administered sequentially under the skin in close proximity or contact.

4. The method according to claim 3, wherein the at least one biocompatible macrocapsule is implanted prior to the autologous source of tumor antigens.

5. The method according to claim 2, wherein the at least one biocompatible macrocapsule is implanted for less than 12 days.

6. The method according to claim 5, wherein the at least one biocompatible macrocapsule is implanted for between 4 and 10 days.

7. The method according to claim 6, wherein the at least one biocompatible macrocapsule is implanted for between 5 and 7 days.

8. The method according to claim 1, wherein the administration comprises multiple injections.

9. The method according to claim 8, wherein the multiple injections occur at regular intervals.

10. The method according to claim 9, wherein, when treatment comprises cancer therapy or vaccination, the regular intervals comprise weekly injections for four weeks followed by two additional immunizations every two weeks.

11. The method according to claim 8, wherein the multiple injections are subcutaneous injections.

12. The method according to claim 1 wherein the said at least one biocompatible macrocapsule has a cylindrical shape and is about 5 to 25 mm, in particular 12 mm in length.

13. The method according to claim 1, wherein the said at least one biocompatible macrocapsule comprises about $8\times10^5$ immuno-isolated allogeneic cells.

14. The method according to claim 1, wherein the said at least one biocompatible capsule comprises one or more of the following: i) a retrieval tube; ii) a retrieval hook secured to the retrieval tube, wherein the retrieval hook facilitates retrieval of the at least one biocompatible macrocapsule after implantation; iii) a connector, wherein the connector secures the membrane of the at least one biocompatible macrocapsule to the retrieval tube; iv) a loading hub, wherein the loading hub facilitates the loading of the cells; and/or v) a transport tube, wherein the transport tube has a tube body and a tube cap.

* * * * *

UNITED STATES PATENT AND TRADEMARK OFFICE
CERTIFICATE OF CORRECTION

PATENT NO. : 11,013,790 B2  
APPLICATION NO. : 15/276016  
DATED : May 25, 2021  
INVENTOR(S) : Nicolas Mach Page 1 of 1

It is certified that error appears in the above-identified patent and that said Letters Patent is hereby corrected as shown below:

In the Specification

Column 11,
Line 41, "IFNα, SCF" should read --IFNγ, SCF--.

Column 19,
Line 30, "IFNα, Stem" should read --IFNγ, Stem--.

Column 26,
Line 1, "CT or MM" should read --CT or MRI--.

Column 32,
Line 62, "to 40 µIL." should read --to 40 µL.--.

Column 33,
Line 46, "STATS A/B" should read --STAT5 A/B--.
Line 46, "STATS TF-1" should read --STAT5 TF-1--.
Line 60, "STATS A/B" should read --STAT5 A/B--.
Line 64, "STATS A/B [pTyr694/6991]–LanthaScreen STATS TF-1" should read --STAT5 A/B [pTyr694/699]–LanthaScreen STAT5 TF-1--.

Column 34,
Line 15, "STATS AB" should read --STAT5 A/B--.

Signed and Sealed this  
Thirtieth Day of November, 2021

Drew Hirshfeld  
*Performing the Functions and Duties of the  
Under Secretary of Commerce for Intellectual Property and  
Director of the United States Patent and Trademark Office*